(12) United States Patent
Holm et al.

(10) Patent No.: US 11,246,761 B2
(45) Date of Patent: Feb. 15, 2022

(54) CONFORMABLE WOUND DRESSING AND DELIVERY SYSTEM

(71) Applicant: 3M INNOVATIVE PROPERTIES COMPANY, Saint Paul, MN (US)

(72) Inventors: David R. Holm, Hudson, WI (US); Richard L. Jacobson, Stillwater, MN (US); Kevin G. Lundquist, Hudson, WI (US); James M. Sieracki, Plymouth, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 234 days.

(21) Appl. No.: 16/338,791

(22) PCT Filed: Oct. 5, 2017

(86) PCT No.: PCT/US2017/055218
§ 371 (c)(1),
(2) Date: Apr. 2, 2019

(87) PCT Pub. No.: WO2018/067758
PCT Pub. Date: Apr. 12, 2018

(65) Prior Publication Data
US 2019/0231604 A1   Aug. 1, 2019

Related U.S. Application Data

(60) Provisional application No. 62/405,631, filed on Oct. 7, 2016.

(51) Int. Cl.
*A61F 13/00* (2006.01)
*A61F 13/02* (2006.01)
(Continued)

(52) U.S. Cl.
CPC ...... *A61F 13/024* (2013.01); *A61F 13/00085* (2013.01); *A61F 13/0236* (2013.01);
(Continued)

(58) Field of Classification Search
None
See application file for complete search history.

(56) References Cited

U.S. PATENT DOCUMENTS

RE24,906 E    12/1960   Ulrich
3,389,827 A    6/1968   Abere
(Continued)

FOREIGN PATENT DOCUMENTS

EP     0552271    4/1996
EP     0507459    4/1999
(Continued)

OTHER PUBLICATIONS

International Search Report for PCT International Application No. PCT/US2017/055218, dated Nov. 23, 2017, 5 pages.
(Continued)

*Primary Examiner* — Kim M Lewis
(74) *Attorney, Agent, or Firm* — 3M Innovative Properties Company

(57) ABSTRACT

Medical articles comprising a conformable wound dressing and delivery system. The wound dressing generally comprises a backing having a first major surface and a second major surface, an adhesive on the second major surface of the backing, and an absorbent pad proximate the second major surface of the backing. The backing extends beyond the perimeter of the absorbent pad, typically beyond the entire perimeter of the pad. The perimeter of the wound dressing has a concave feature that exhibits a local minimum. An axis extends from the local minimum to the perimeter of the wound dressing opposite the local mini-
(Continued)

mum. The carrier overlies at least a portion of the backing on each side of the axis but does not overlie the backing along the axis. The wound dressing is especially designed for use on round or irregular shaped body parts, such as an elbow or heel.

18 Claims, 18 Drawing Sheets

(51) Int. Cl.
*A61F 13/06* (2006.01)
*A61F 13/10* (2006.01)

(52) U.S. Cl.
CPC .......... *A61F 13/061* (2013.01); *A61F 13/064* (2013.01); *A61F 13/101* (2013.01); *A61F 2013/00608* (2013.01); *A61F 2013/00817* (2013.01); *A61F 2013/00834* (2013.01)

(56) References Cited

U.S. PATENT DOCUMENTS

| | | | |
|---|---|---|---|
| 3,645,835 | A | 2/1972 | Hodgson |
| 4,112,213 | A | 9/1978 | Waldman |
| 4,310,509 | A | 1/1982 | Berglund |
| 4,323,557 | A | 4/1982 | Rosso |
| 4,472,480 | A | 9/1984 | Olson |
| 4,499,896 | A | 2/1985 | Heinecke |
| 4,598,004 | A | 7/1986 | Heinecke |
| 4,737,410 | A | 4/1988 | Kantner |
| 5,088,483 | A | 2/1992 | Heinecke |
| 5,160,315 | A | 11/1992 | Heinecke |
| 5,531,855 | A | 7/1996 | Heinecke |
| 5,622,711 | A | 4/1997 | Chen |
| 5,633,010 | A | 5/1997 | Chen |
| 5,738,642 | A | 4/1998 | Heinecke |
| 5,849,325 | A | 12/1998 | Heinecke |
| 6,169,224 | B1 | 1/2001 | Heinecke |
| 6,171,985 | B1 | 1/2001 | Joseph |
| 6,368,687 | B1 | 4/2002 | Joseph |
| 6,436,432 | B2 | 8/2002 | Heinecke |
| 6,838,589 | B2 | 1/2005 | Liedtke |
| 2010/0106120 | A1 | 4/2010 | Holm |
| 2010/0260824 | A1* | 10/2010 | Shah ................. A61P 17/02 424/447 |
| 2016/0038345 | A1* | 2/2016 | Ha ................... A61F 13/02 602/46 |

FOREIGN PATENT DOCUMENTS

| | | |
|---|---|---|
| WO | WO 1999-027975 | 6/1999 |
| WO | WO 2007-034393 | 3/2007 |
| WO | WO 2010/048480 | 4/2010 |
| WO | WO 2010-056541 | 5/2010 |
| WO | WO 2010-056543 | 5/2010 |
| WO | WO 2010/147930 | 12/2010 |
| WO | WO 2013-162680 | 10/2013 |
| WO | WO 2013/162680 | 10/2013 |
| WO | WO 2015-102981 | 7/2015 |

OTHER PUBLICATIONS

Satas, Handbook of Pressure Sensitive Adhesive Technology, 384-403 (1982).

* cited by examiner

CONFORMABLE WOUND DRESSING AND DELIVERY SYSTEM

CROSS REFERENCE TO RELATED APPLICATIONS

This application is a national stage filing under 35 U.S.C. 371 of PCT/US2017/055218, filed Oct. 5, 2017, which claims the benefit of U.S. Provisional Application No. 62/405,631, filed Oct. 7, 2016, the disclosures of which are incorporated by reference in their entirety herein.

FIELD OF INVENTION

The present invention relates to medical articles having a combined wound dressing and delivery system. The dressing is particularly useful for application to wounds on rounded or irregularly shaped body parts, such as heels and elbows.

BACKGROUND

Wound dressings using an absorbent central area surrounded by a larger adhesive film are known. For example, U.S. Pat. No. 5,738,642 (the '642 patent) shows a wound dressing and delivery system comprising a thick absorbent pad placed in the center of a thin backing. A carrier frame surrounds the perimeter of the wound dressing, providing sufficient support (e.g. rigidity) to the backing to facilitate handling of the dressing during application to a wound. The dressing taught in the '642 patent is useful for application to a large variety of wounds. In another example, U.S. Pat. No. 6,838,589 (the '589 patent) shows a wound dressing comprising a centrally located absorbent pad and a dressing support layer. The dressing support layer has a radial configuration that forms a plurality of alternating covered and uncovered portions of the backing layer along the perimeter of the wound dressing. The wound dressing and delivery system of the '589 patent are particularly well suited to application over a convex surface of a patient, such as a patient's heel.

Despite the advances in wound dressing described above, there is still a need for wound dressings that are easy to use, conform well to rounded or irregularly shaped surfaces, and provide a secure seal to maintain a sterile environment at the wound site.

SUMMARY

The present disclosure describes medical articles comprising a wound dressing and delivery system (or carrier). The wound dressing is especially designed for use as a heel or elbow dressing, although the dressing is not limited to these applications and can be used to cover wounds on other anatomical parts.

The wound dressing generally comprises an absorbent pad, a backing, and an adhesive on the major surface of the backing facing the absorbent pad. Preferably the adhesive backing forms a border around the absorbent pad to create an island dressing. The adhesive coated backing is relatively thin and generally very flexible. A carrier is applied to the backing to prevent the border of the dressing from folding over or adhering to itself prior to and during application to the wound site.

The perimeter of the dressing has one or more concave features that make it easier to secure the dressing about rounded or irregular body parts. A user positions the dressing over a wound, secures a section of the dressing at the wound site, and then wraps the remaining sections of the dressing around the wound site so that the dressing overlaps, creating a relatively wrinkle free dressing with a secure border seal. The carrier is designed to support the more flexible portions of the dressing while permitting sufficient conformability for securement of the dressing to rounded or other irregularly shaped body parts. The carrier is removed from the wound dressing during and/or immediately after securement to the wound site.

In one embodiment, the present disclosure provides a medical article comprising a wound dressing and a carrier. The wound dressing comprises a backing having a first major surface and a second major surface, an adhesive on the second major surface of the backing, and an absorbent pad having a first major surface and a second major surface, where the first major surface of the absorbent pad is proximate the second major surface of the backing. The backing extends beyond the perimeter of the absorbent pad. The perimeter of the wound dressing has a concave feature that exhibits a local minimum. An axis extends from the local minimum to the perimeter of the wound dressing opposite the local minimum. A carrier that comprises at least two carrier strands is removably attached to the first major surface of the backing. The carrier overlies at least a portion of the backing on each side of the axis but does not overlie the backing along the axis.

In another embodiment, the present disclosure provides a medical article comprising a wound dressing and a carrier. The wound dressing comprises a backing having a first major surface and a second major surface, an adhesive on the second major surface of the backing, and an absorbent pad having a first major surface and a second major surface, where the first major surface of the absorbent pad is proximate the second major surface of the backing. The backing extends beyond the perimeter of the absorbent pad. The dressing comprises a first concave feature having a first local minimum and a second concave feature having a second local minimum, wherein the second concave feature is located opposite the first concave feature. A first axis extends across the wound dressing from the first local minimum to the second local minimum. A carrier that comprises at least two carrier strands is removably attached to the first major surface of the backing. The carrier overlies at least a portion of the backing on each side of the axis but does not overlie the backing along the axis.

In a further embodiment, the present disclosure provides a medical article comprising a wound dressing and a carrier. The wound dressing comprises a backing having a first major surface and a second major surface, an adhesive on the second major surface of the backing, and an absorbent pad having a first major surface and a second major surface, where the first major surface of the absorbent pad is proximate the second major surface of the backing. The backing extends beyond the perimeter of the absorbent pad. The dressing further comprises a first concave feature having a first local minimum and a second concave feature having a second local minimum, wherein the second concave feature is located opposite the first concave feature. A first axis extends across the wound dressing from the first local minimum to the second local minimum. The wound dressing additionally comprises a third concave feature having a third local minimum and a fourth concave feature having a fourth local minimum, wherein the third concave feature is located opposite the fourth concave feature and a second axis extends across the wound dressing from the third local minimum to the fourth local minimum. The second axis is substantially perpendicular to the first axis. A carrier overlies at least a portion of the backing in each quadrant bordered by the first and second axes but does not overlie the backing along either of the first or second axes.

The above summary of the present disclosure is not intended to describe each disclosed embodiment or every implementation of the present disclosure. The description that follows more particularly exemplifies illustrative embodiments.

With reference to the figures, like reference numbers offset by multiples of 100 (e.g., 18, 118, 218) indicate like elements. Some elements may be present in similar or identical multiples; in such cases the elements may comprise the same reference number, with one or more of the elements designated by a letter (e.g., a, b, c, d) for convenience of description. Unless otherwise indicated, all figures and drawings in this document are not to scale and are chosen for the purpose of illustrating different embodiments of the invention. In particular, the dimensions of the various components are depicted in illustrative terms only, and no relationship between the dimensions of the various components should be inferred from the drawings, unless so indicated.

DETAILED DESCRIPTION

Before any embodiments of the present disclosure are explained in detail, it is to be understood that the phraseology and terminology used herein is for the purpose of description and should not be regarded as limiting. As used herein, the terms "including," "comprising," or "having" and variations thereof encompass the items listed thereafter and equivalents thereof, as well as additional items. All numerical ranges are inclusive of their endpoints and non-integral values between the endpoints unless otherwise stated. Terms such as "front surface" and "back surface" used with respect to the backing, absorbent pad, the facing layer, and any other components in the medical articles, refer to the major surface of the indicated component that, in use, faces toward the wound surface or away from the wound surface, respectively. As used herein, the term "overlie" or "overlap" means to extend over so as to at least partially cover another layer or element. Overlying layers can be in direct or indirect contact (e.g., separated by one or more additional layers).

FIGS. 1-3 generally relate to medical articles comprising a wound dressing and a carrier. The wound dressing of the present invention is preferably an island dressing having a relatively rigid absorbent pad surrounded by a more flexible adhesive backing laminate. The wound dressing is especially designed for use as a heel or elbow dressing, although the dressing is not limited to these applications and can be used to cover wounds on other anatomical parts. The carrier is designed to support the more flexible portions of the dressing and can be removed in stages to provide enhanced conformability during application to rounded or other irregularly shaped body parts. The carrier can also be configured with tabs that aid the user in positioning, applying, and securing the dressing about the wound site.

Figure 1A:
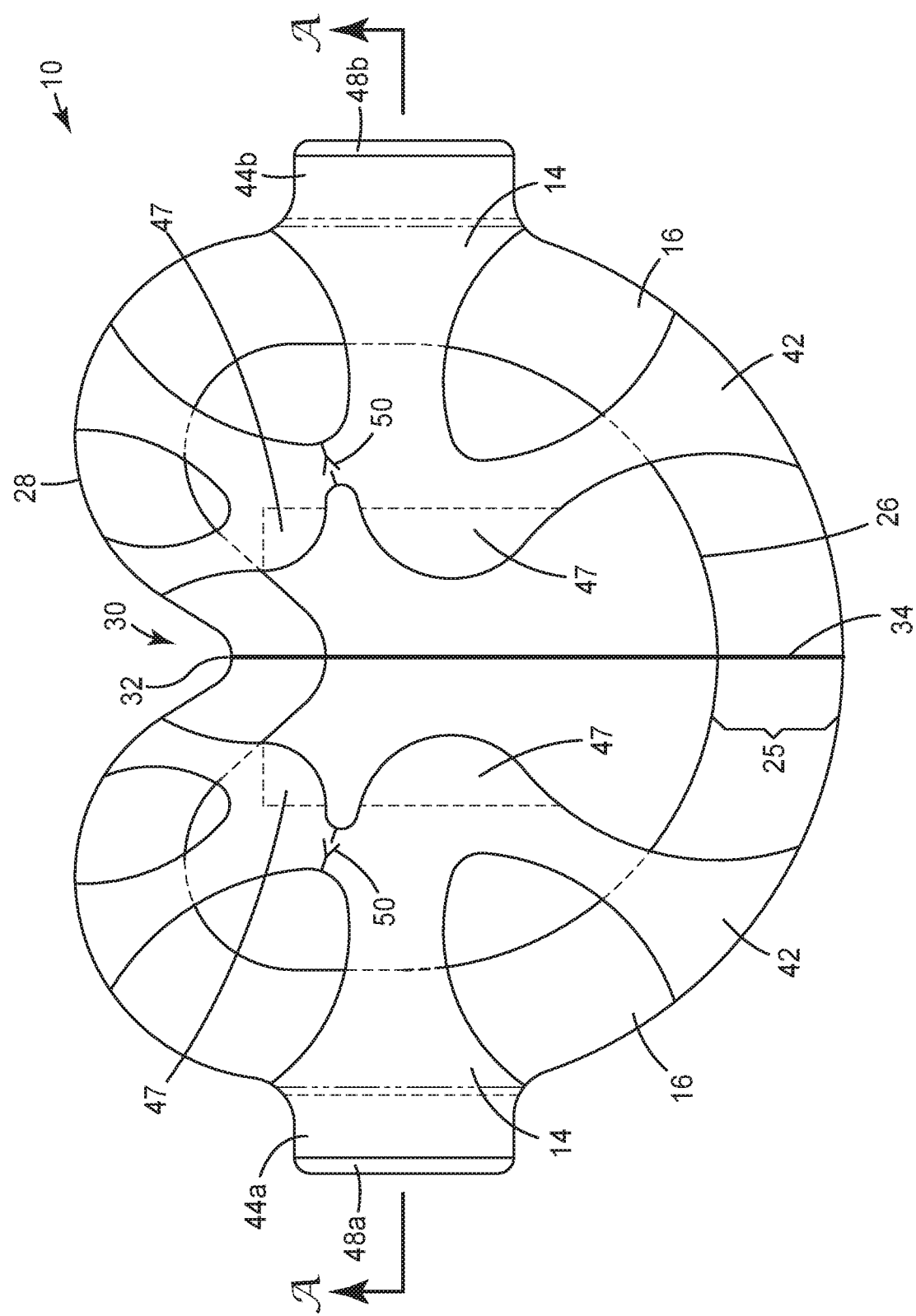
FIG. 1A is a schematic top plan view of one embodiment of a combined wound dressing and delivery system in the present disclosure.
Figure 1B:
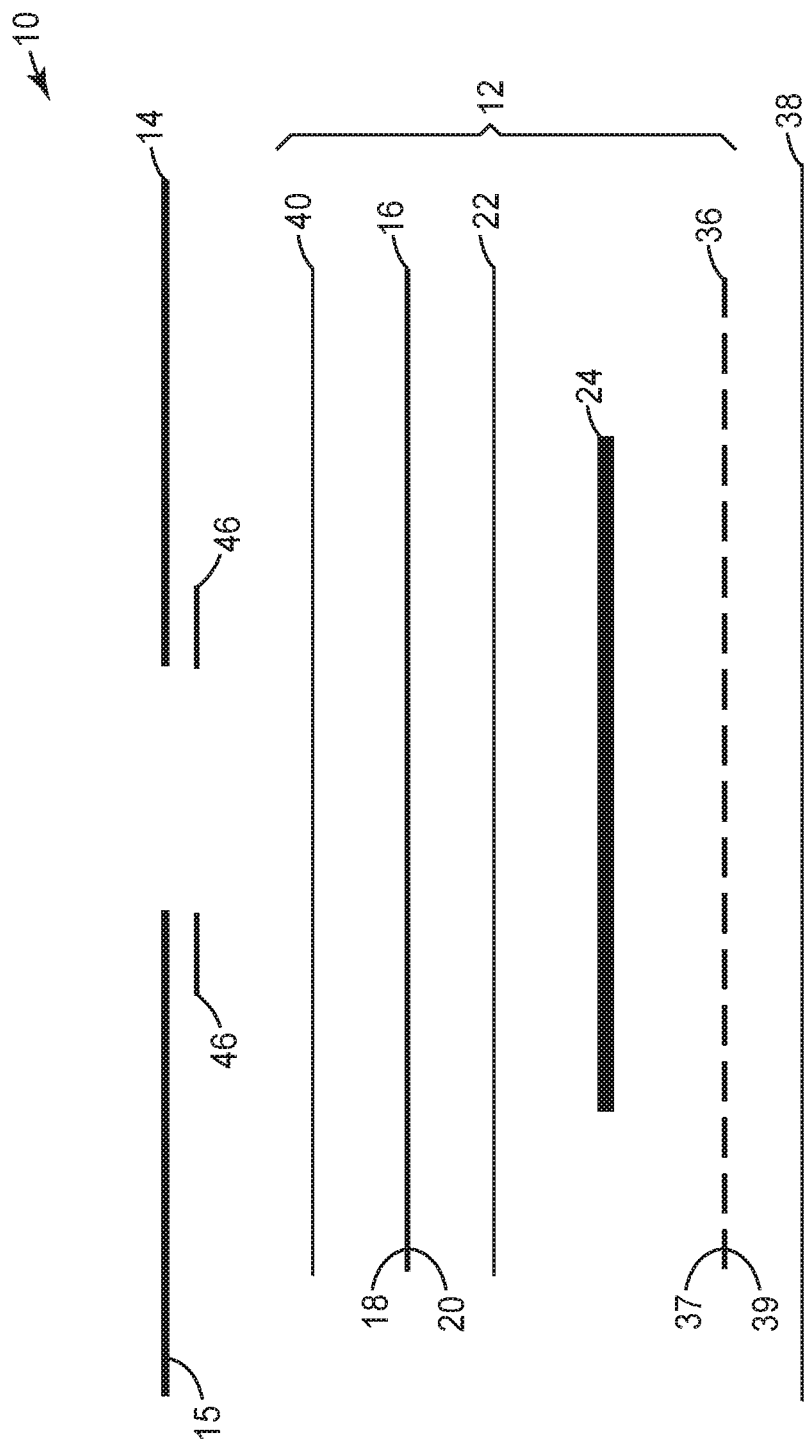
FIG. 1B is a schematic cross-sectional view of the combined wound dressing and delivery system taken along line A-A in FIG. 1A.

FIGS. 1A & 1B illustrate one embodiment of a medical article 10 in the present disclosure. The medical article 10 comprises a wound dressing 12 having a general kidney shape and a delivery system or carrier 14.

The wound dressing 12 generally comprises a backing 16 having a first major surface 18 and a second major surface 20, an adhesive 22 on the second major surface 20 of the backing 16, and an absorbent pad 24 proximate the second major surface 20 of the backing 16. Although the absorbent pad 24 is adhesively bonded to the second major surface 20 of the backing 16, other configurations are contemplated. For example, the adhesive may extend over only a portion of the backing opposite the absorbent pad, leaving some regions of the absorbent pad adhesive free or, with a facing layer (described below), the pad can be retained next to the backing without actually being attached, or bonded, to the backing. Returning to FIGS. 1A & B, the backing 16 extends beyond the perimeter 26 of the absorbent pad 24 to create a dressing border 25. Preferably, the backing 16 extends beyond the entire perimeter 26 of the absorbent pad 24 to form an island dressing. The perimeter 28 of the wound dressing 12 has a concave feature 30 that exhibits a local minimum 32. An axis 34 extends from the local minimum 32 of the concave feature 30 to the perimeter 28 of the wound dressing 12 opposite the local minimum 32. Although the absorbent pad 24 and backing 16 of the wound dressing 12 in FIG. 1A are similarly shaped, it is not necessary. Similarly, the wound dressing can be symmetrical about the axis 34, as illustrated in FIG. 1A, or unsymmetrical.

A low adhesion coating (low adhesion backsize or LAB) 40 is optionally provided on the first major surface 18 of the backing 16 such that the low adhesion coating 40 is sandwiched between at least a portion of the carrier 14 and the first major surface 18 of the backing 16. The low adhesion coating can cover the entire first major surface of the backing or partially cover the first major surface of the backing (e.g., pattern coated). A suitable low adhesion coating for use in the present dressings can be found, for example, in U.S. Pat. No. 5,531,855 (Example 1), which is compatible with a heat seal bond as described below. The low adhesion coating reduces dressing changes due to unwanted dressing removal when other tapes or devices are placed on the dressing and removed, and reduces the surface friction of the dressing on linen or other fabrics, thereby offering additional protection against the accidental removal of the dressing.

The wound dressing may optionally include a facing layer 36 having a first major surface 37 and a second major surface 39. The first major surface 37 of the facing layer is proximate the absorbent pad 24. In one embodiment, as illustrated in FIGS. 1A & 1B, the facing layer 36 may be contiguous with the backing 16 and adhere to the adhesive 22 at the dressing border 25, thus forming a pouch that contains the absorbent pad 24. The facing layer may have an adhesive on the first major surface and adhesively bond to at least a portion of the absorbent pad. Alternatively, or additionally, the facing layer may have an adhesive on the second major surface and bond directly to the skin at the wound site. The facing layer is preferably soft, flexible, conformable, non-irritating, non-sensitizing, and liquid permeable. In a preferred embodiment, the facing layer is a perforated adhesive/film/adhesive laminate.

The carrier 14 comprises at least two carrier strands 42 removably attached to the first major surface 18 of the backing 16 that has been preferably treated with a low adhesion coating. The carrier 14 overlies at least a portion of the backing 16 on each side of the axis 34. However, the carrier 14 does not overlie the backing 16 along the axis 34. In some embodiments, 5-50%, more particularly 10-30%, of the backing first major surface 18 surrounding the axis 34 is free of carrier 14. In alternative embodiments, the backing first major surface 18 within 0.48 cm (3/16 inch), more preferably 0.64 cm (1/4 inch), of each side of the axis 34 measured in a direction perpendicular to the axis 34 is free of carrier 14. By eliminating carrier entirely from the center of the dressing along the axis, the wound dressing can be easily bent and/or twisted to conform to irregularly shaped body parts.

The carrier 14 in FIGS. 1A & 1B overlies at least a portion of the absorbent pad 24 and extends to the perimeter 28 of the wound dressing 12, overlying some, but not all, of the dressing border 25. The dressing border 25 that is adhesively secured to a patient is not supported or reinforced by the relatively heavy and stiff absorbent pad 24. Absent the carrier 14, the border 25 would be difficult to handle without folding, wrinkling or otherwise adhering to itself rather than adhering to the skin. On the other hand, the carrier 14 is made of a stiffer material than the backing 16 and can actually reduce the flexibility and conformity of the dressing. To balance these two competing effects, the carrier 14 overlies some but not all of the dressing border 25. In some embodiments, the carrier overlies 5-50% of the region defined by the dressing border. In other embodiments, the carrier overlies 5-30% of the region defined by the dressing border.

A portion of the carrier 14 overlying the absorbent pad 24 may optionally include a bond block 46 on a major surface 15 facing the backing 16. The bond block 46 prevents attachment of that portion of the carrier 14 to the backing 16, creating tabs 47 that facilitate removal of the carrier 14 by a user. The user simply grabs a tab 47 and peels the carrier 14 back towards the perimeter 28 of the wound dressing 12.

The carrier 14 illustrated in FIG. 1A is made up of two carrier strands 42. Each strand can be a single unified structure. Or, as in FIG. 1A, one or more strands are provided with precut paths 50 dividing the strands into smaller segments. The paths or lines 50 provide controlled tear of the dressing carrier 14 when tabs 47 are lifted to remove the carrier 14 during and/or after application of the dressing 12 to a patient. The configuration of the path or lines includes, but is not limited to, linear, angled, Y-shaped, dual-angled offset, circular holes and alternating combination thereof. Instead of precut paths, a similar effect can be achieved by using two or more smaller carrier strands in place of one larger, precut strand.

The carrier can also be used to position and apply a dressing to a wound site using two or more tabs. In FIG. 1A, the carrier 14 on each side of the axis 34 extends past the perimeter 28 of the wound dressing 12 to form a tab 44a, 44b. The tab 44a on one side of the axis 34 is preferably located substantially opposite the tab 44b on the other side of the axis 34. Both tabs 44a, 44b extend in a direction substantially perpendicular to the axis 34. In practice, the user holds a tab in each hand, aligns the dressing over the wound site, and then uses the tabs to wrap and secure the dressing about the wound. The tabs are then removed as part of the carrier.

In addition to the wound dressing 12 and carrier 14, the article 10 also comprises a release liner 38 that is attached to the exposed adhesive on the front surface of the dressing. The release liner 38 covers the adhesive until the user is ready to apply the dressing to the wound site. Depending upon the configuration of the dressing, the release liner may cover adhesive on the backing, facing layer, or a combination of both. The release liner 38 may be a single piece or multiple pieces, and may be part of, or laminated to, the package (not shown) containing the dressing, or merely enclosed along with the dressing 12 within the package. In FIG. 1A, the release liner 38 extends beyond the carrier tabs 44a, 44b to form release tabs 48a, 48b. The tabs 48a, 48b of the release liner and the tabs 44a, 44b of the carrier are at least partially unattached. The bond between the carrier 14 and the backing 16 is stronger than the bond between the adhesive and the release liner 38 so that the backing 16 remains attached to the carrier 14 when the release liner 38 is removed from the dressing 12.

Figure 5A:
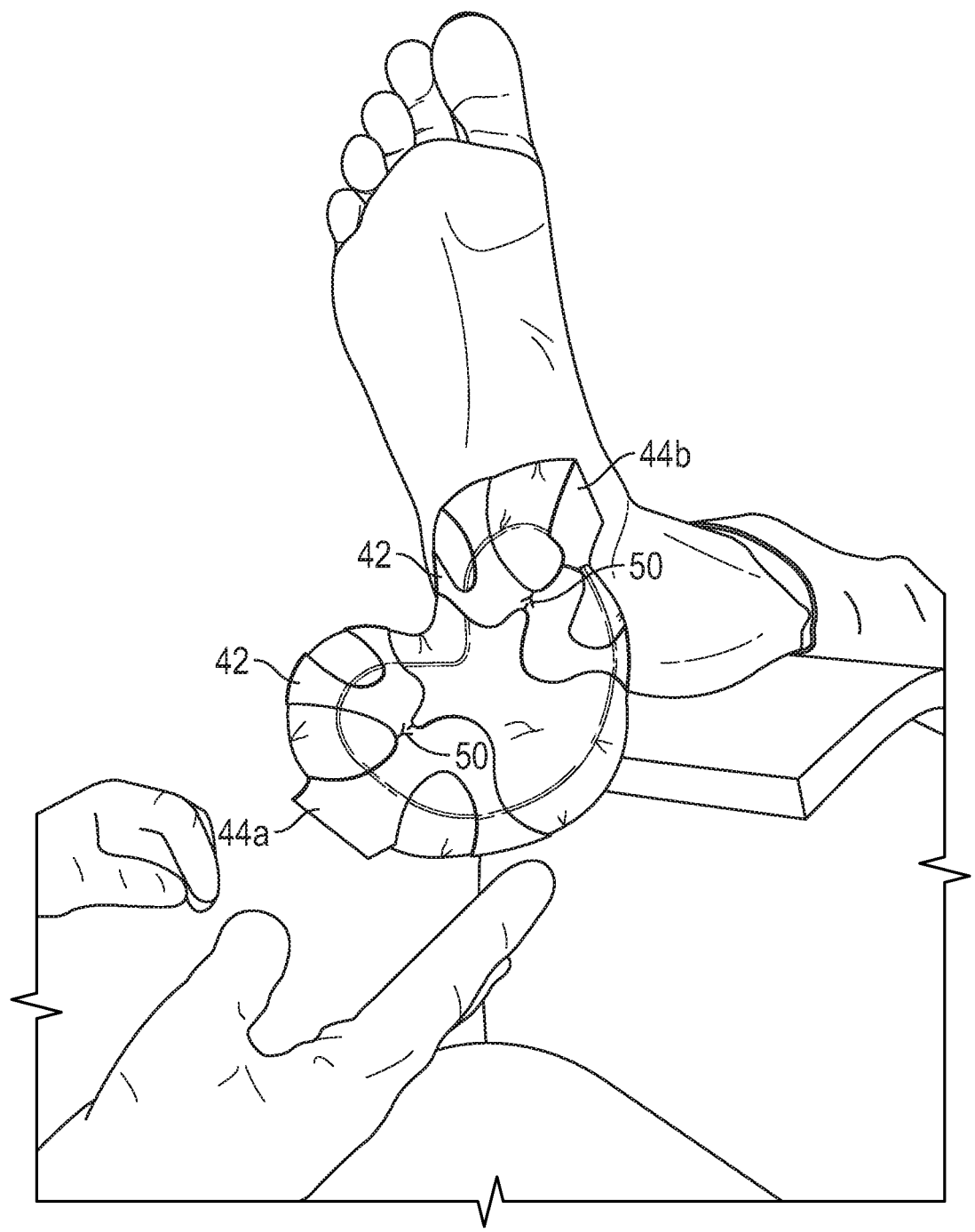
FIGS. 5A-E illustrate one application of the combined wound dressing and delivery system of FIGS. 1A and 1B.
Figure 5B:
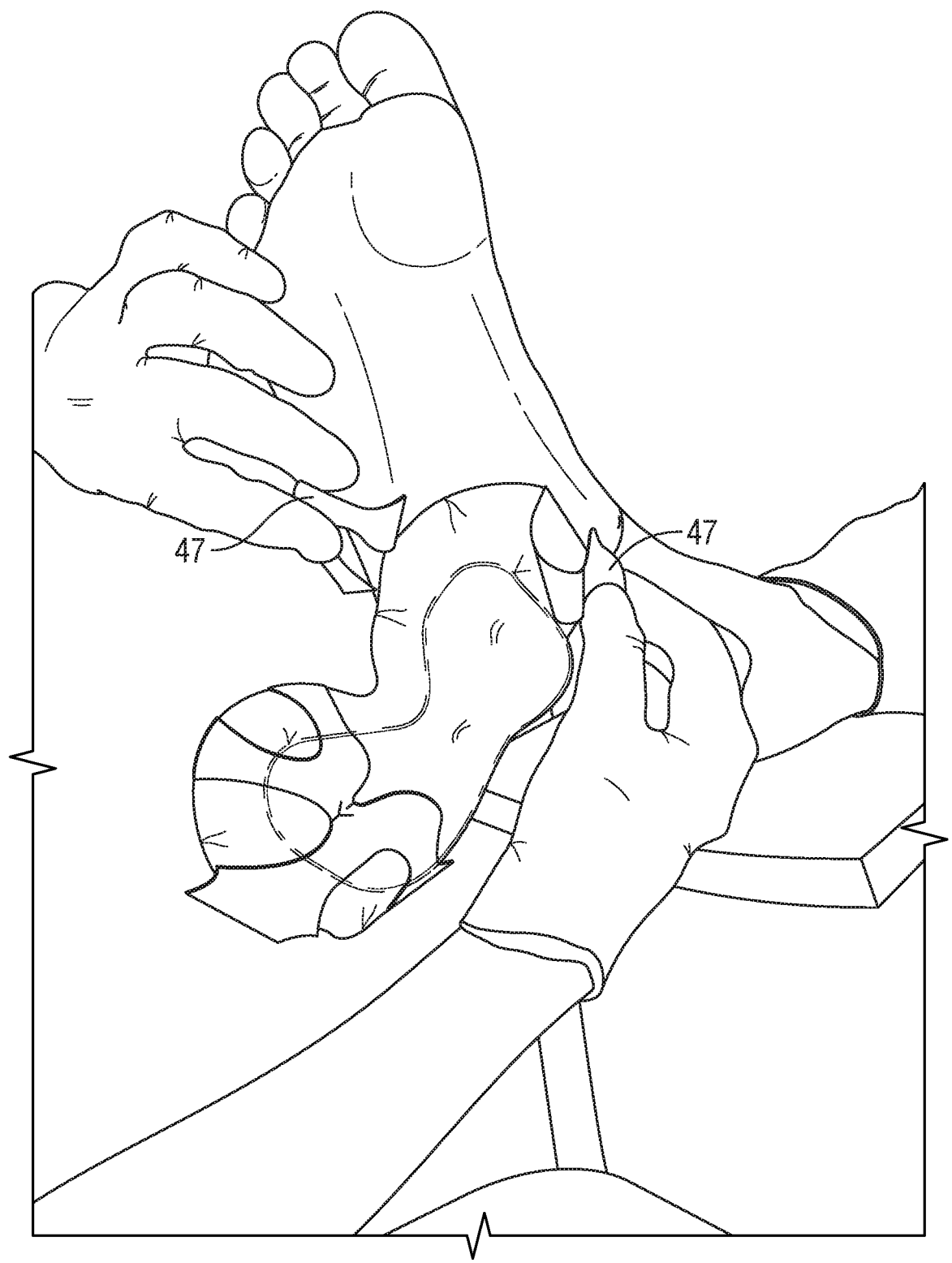
Figure 5C:
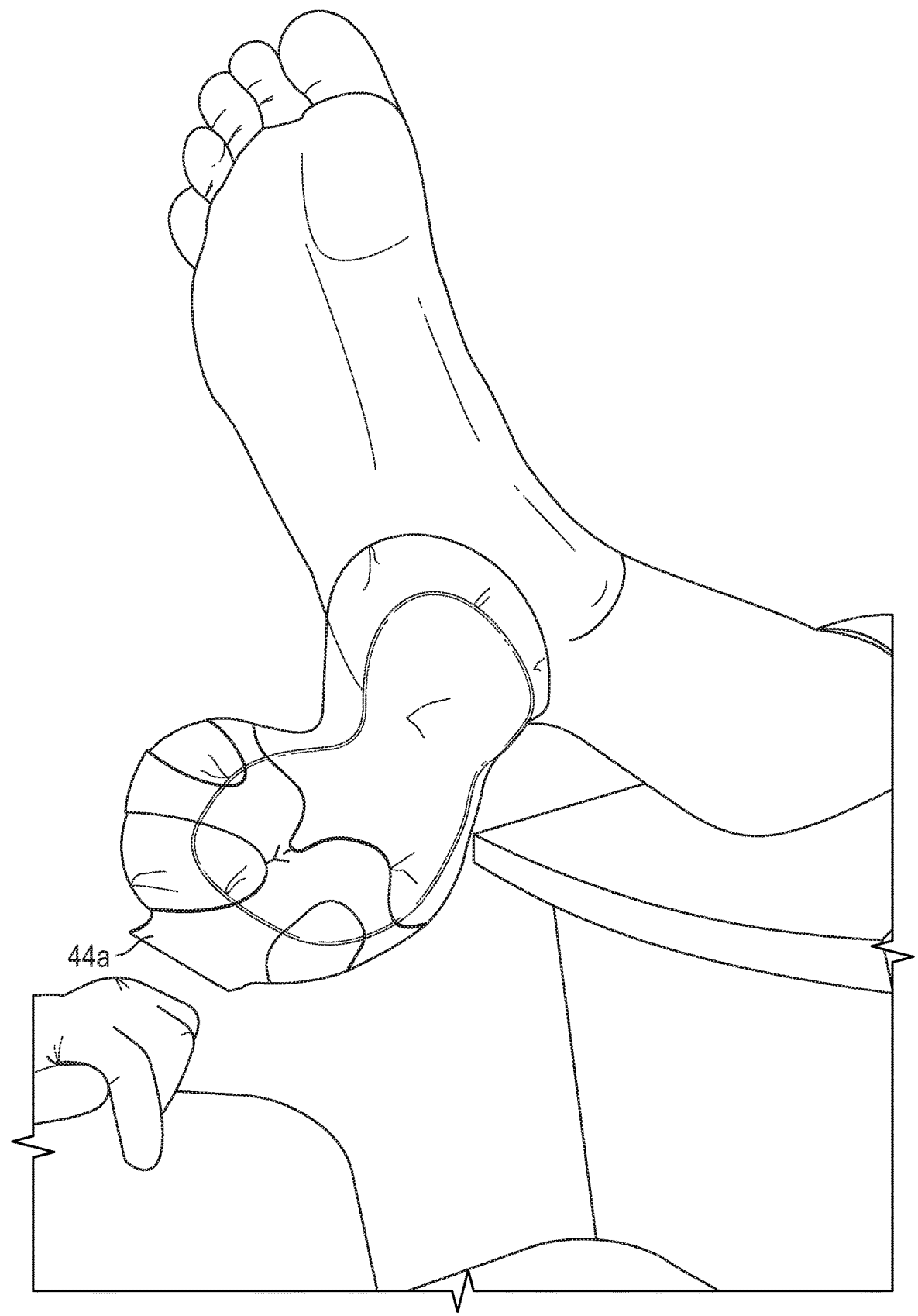
Figure 5D:
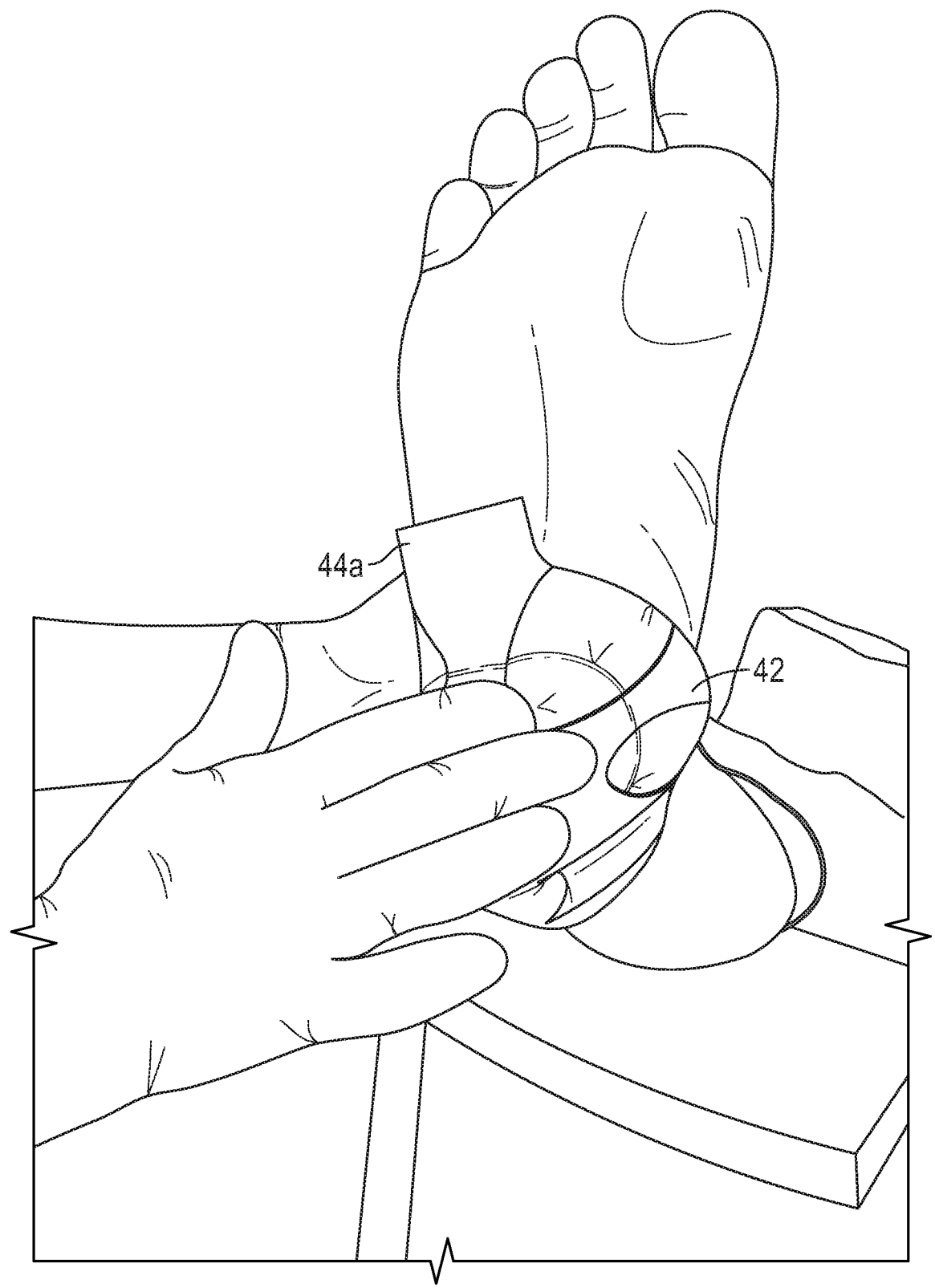
Figure 5E:
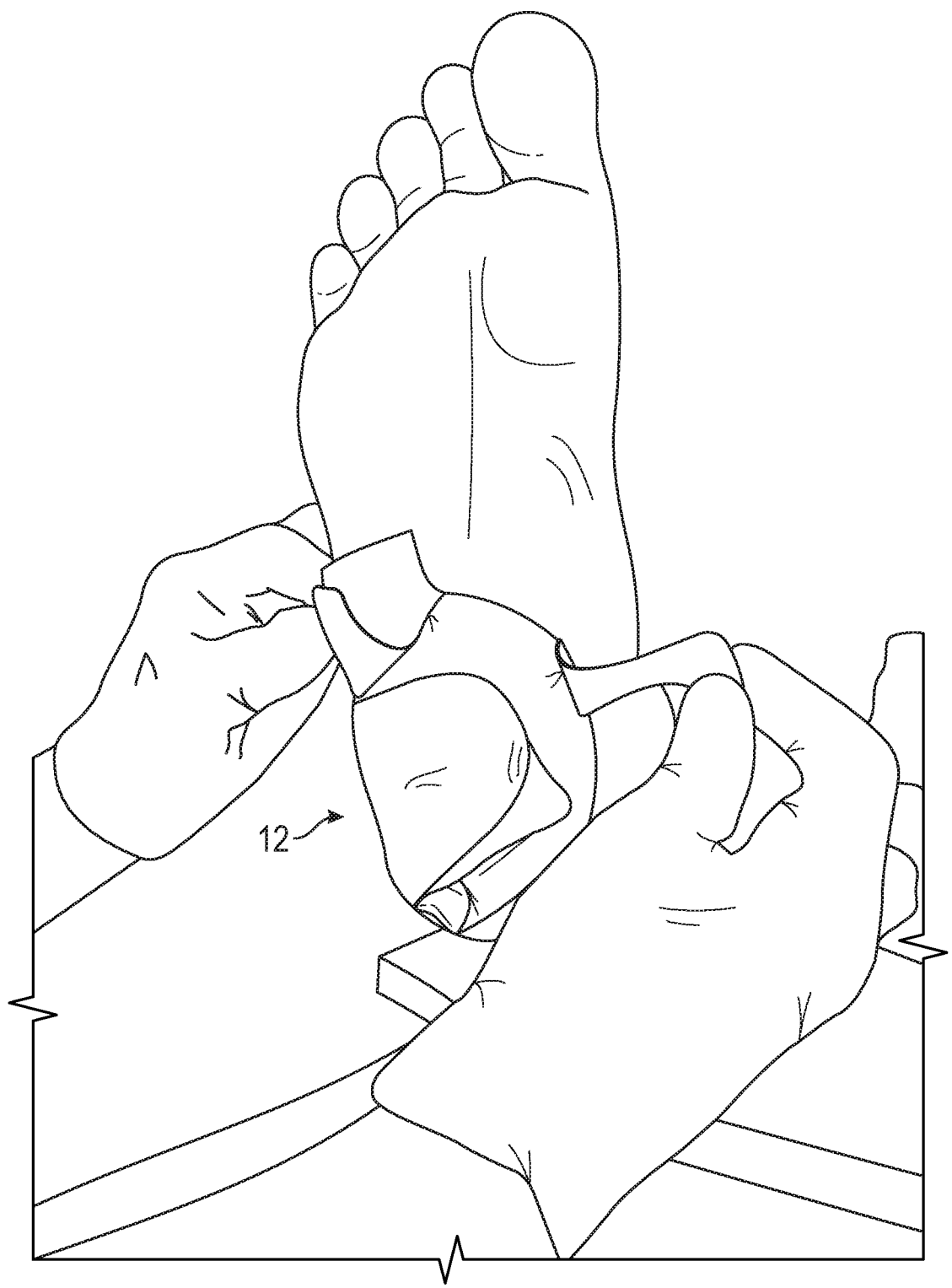

FIGS. 5A-E illustrate one way to dress a heel wound using the medical article illustrated in FIGS. 1A and 1B. With the release liner already removed, the user applies one side of the dressing just above and to the right of the center of the heel. The tab 44b can be used to position the dressing in place. The user then removes the carrier strand 42 over the region of the dressing attached to the heel by grabbing tabs 47 and peeling each section of strand 42 back towards the perimeter of the dressing. In some instances, the bending of the dressing will break the precut path 50 (if not already broken) causing the tabs 47 to rise off the first major surface of the backing, facilitating removal of the carrier strand 42 from the wound dressing. Removal of a portion of the carrier increases the flexibility of the wound dressing to more freely wrap about the heel and prevents pinning of the carrier between overlapping section of the dressing. In FIGS. 5C and 5D, the user grabs tab 44a and wraps the remaining portion of the dressing around the heel so that the dressing overlaps on itself to produce a relatively smooth dressing with a secure border to protect the wound site. The remaining carrier strand 42 is then removed as shown in FIG. 5E.

Figure 2A:
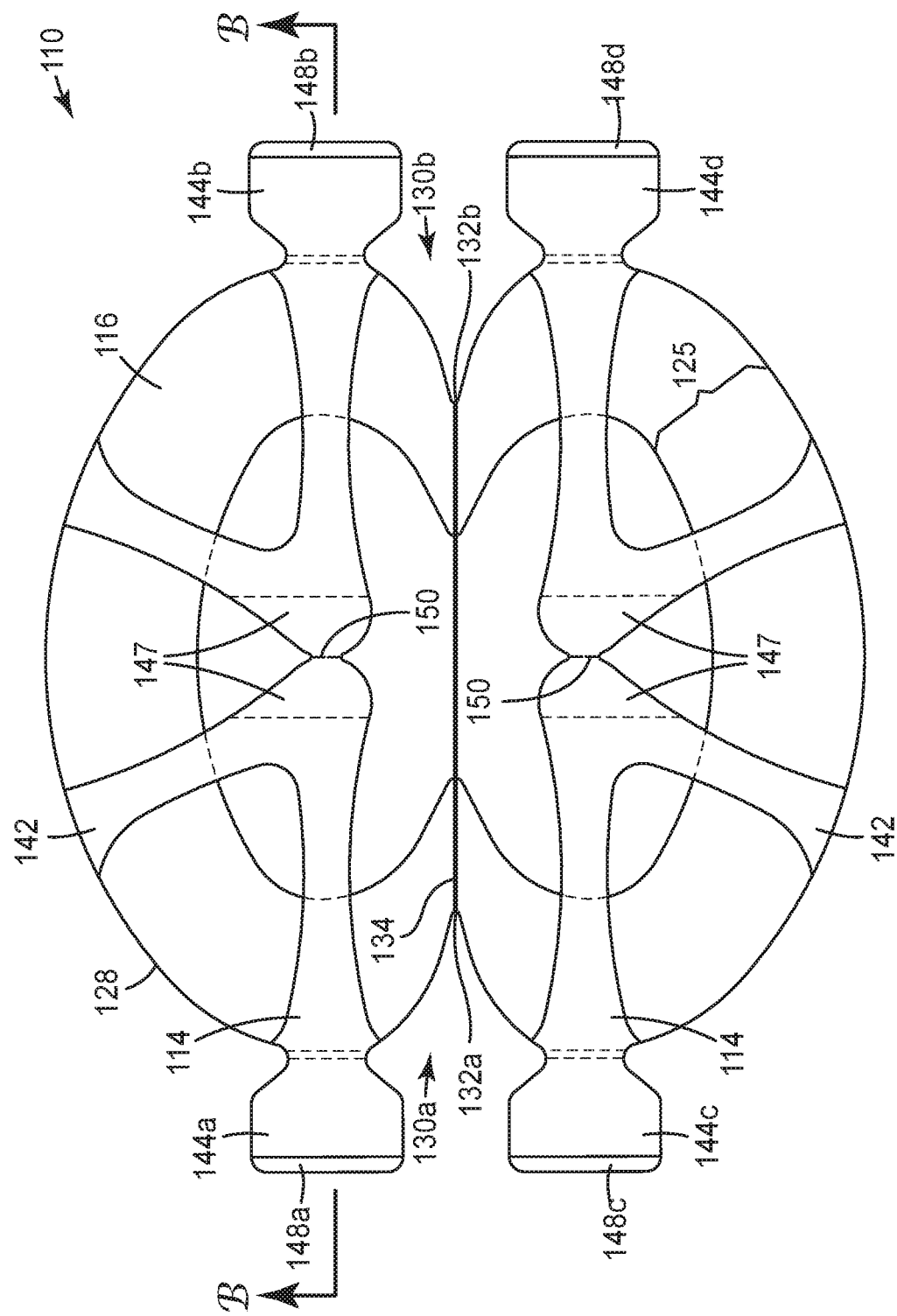
FIG. 2A is a schematic top plan view of a second embodiment of a combined wound dressing and delivery system in the present disclosure.
Figure 2B:
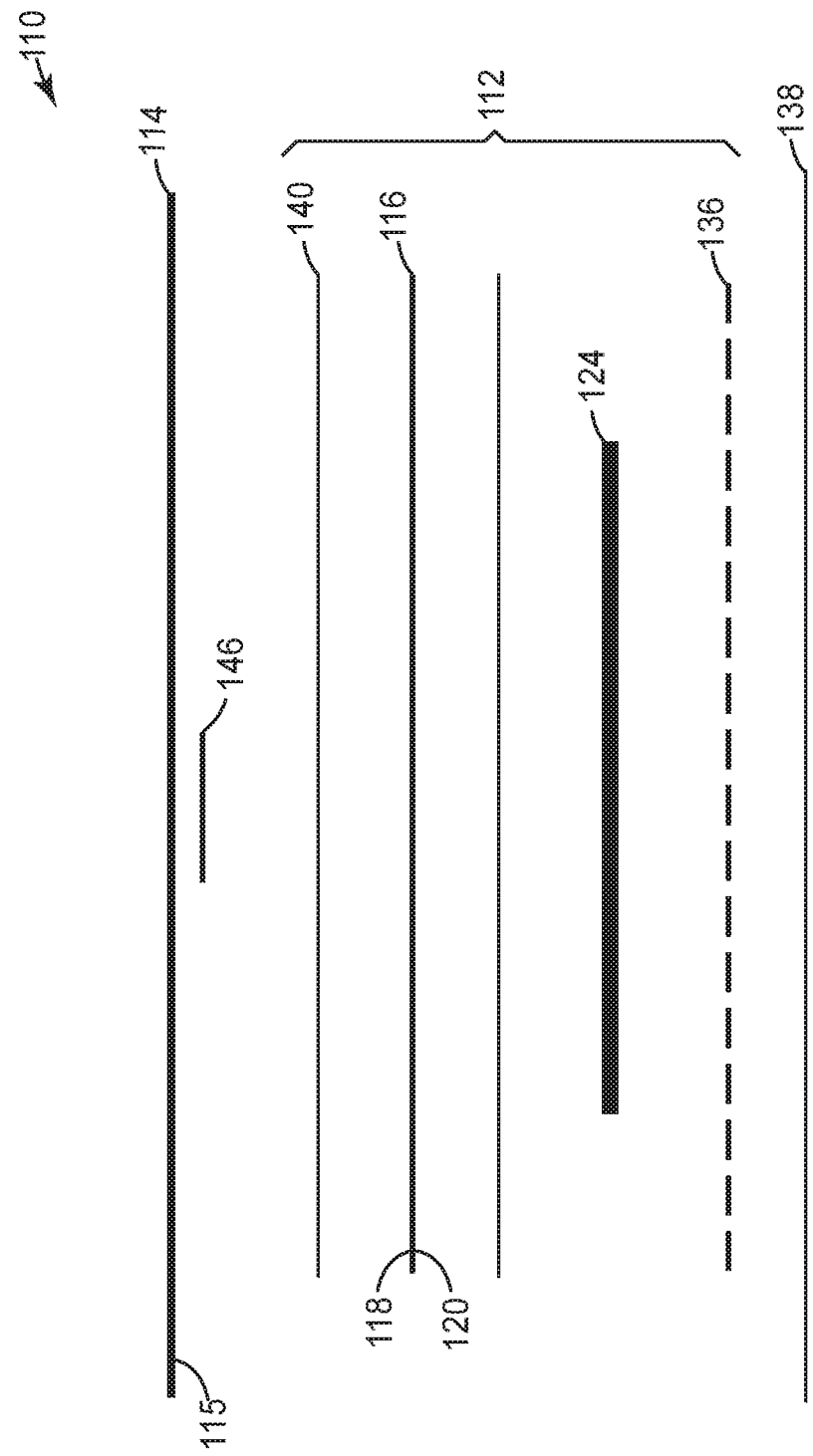
FIG. 2B is a schematic cross-sectional view of the combined wound dressing and delivery system taken along line B-B in FIG. 2A.

FIGS. 2A & 2B illustrate a second embodiment of a medical article 110 in the present disclosure. The medical article 110 comprises a wound dressing 112 having a two lobe configuration and a delivery system or carrier 114. The wound dressing 112 has a similar layered configuration to that described above with respect to FIGS. 1A & 1B but differs in that the dressing 112 in FIG. 2A has an additional concave feature on the perimeter 128 of the dressing 112. The first concave feature 130a has a first local minimum 132a, and the second concave feature 130b has a second local minimum 132b. The first concave feature 130a is located opposite the second concave feature 130b. An axis 134 extends across the wound dressing 112 from the first local minimum 132a of the first concave feature 130a to the second local minimum 132b of the second concave feature 130b.

The carrier 114 comprises at least two carrier strands 142 removably attached to the first major surface 118 of the backing 116 that has been preferably treated with a low adhesion coating. Each strand 142 can be a single unified structure. Or, as illustrated in FIG. 2A, one or more strands are provided with precut paths 150 so that the carrier is removed in smaller segments. A similar effect can be achieved by using two or more smaller carrier strands in place of one larger, precut strand. The carrier 114 overlies at least a portion of the backing 116 on each side of the axis 134. However, the carrier 114 does not overlie the backing 116 along the axis 134. In some embodiments, 5-50%, more particularly 10-30%, of the backing first major surface 118 surrounding the axis 134 is free of carrier 114. In alternative embodiments, the backing first major surface 118 within 0.48 cm (3/16 inch), more preferably 0.64 cm (1/4 inch), of each side of the axis 134 measured in a direction perpendicular to the axis 134 is free of carrier 114.

The carrier 114 in FIG. 2A overlies at least a portion of the absorbent pad 124 and extends to the perimeter 128 of the wound dressing 112, overlying some, but not all, of the dressing border 125. In some embodiments, the carrier overlies 5-50% of the region defined by the dressing border. In other embodiments, the carrier overlies 5-30% of the region defined by the dressing border.

A portion of the carrier 114 overlying the absorbent pad 124 may optionally include a bond block 146 on a major surface 115 facing the backing 116. The bond block 146 prevents attachment of that portion of the carrier 114 to the backing 116 and creates tabs 147 that facilitate removal of the carrier 114 by a user. The user simply grabs a tab 147 and peels the carrier 114 back towards the perimeter 128 of the dressing 112.

The carrier can also be used to position and apply a dressing to a wound site using two or more tabs. In FIG. 2A, the carrier 114 on each side of the axis 134 extends past the perimeter 128 of the wound dressing 112 to form one tab 144a, 144c located substantially opposite another tab 144b, 144d. Each tab 144a, 144b, 144c, 144d extends in a direction that is substantially parallel to the axis 134a. In practice, the user aligns the dressing over the wound site, and then uses the tabs to wrap and secure the dressing about the wound. The tabs are then removed as part of the carrier.

As illustrated in FIG. 2B, the release liner 138 is attached to the exposed adhesive on the front surface of the dressing 112 and extends beyond the carrier tabs 144a, 144b, 144c, 144d to form release tabs 148a, 148b, 148c, 148d. The tabs 148a, 148b, 148c, 148d of the release liner and the tabs 144a, 144b, 144c, 144d of the carrier are at least partially unattached, allowing for easy separation of the release liner 138 from the carrier 114 and wound dressing 112.

Figure 6A:
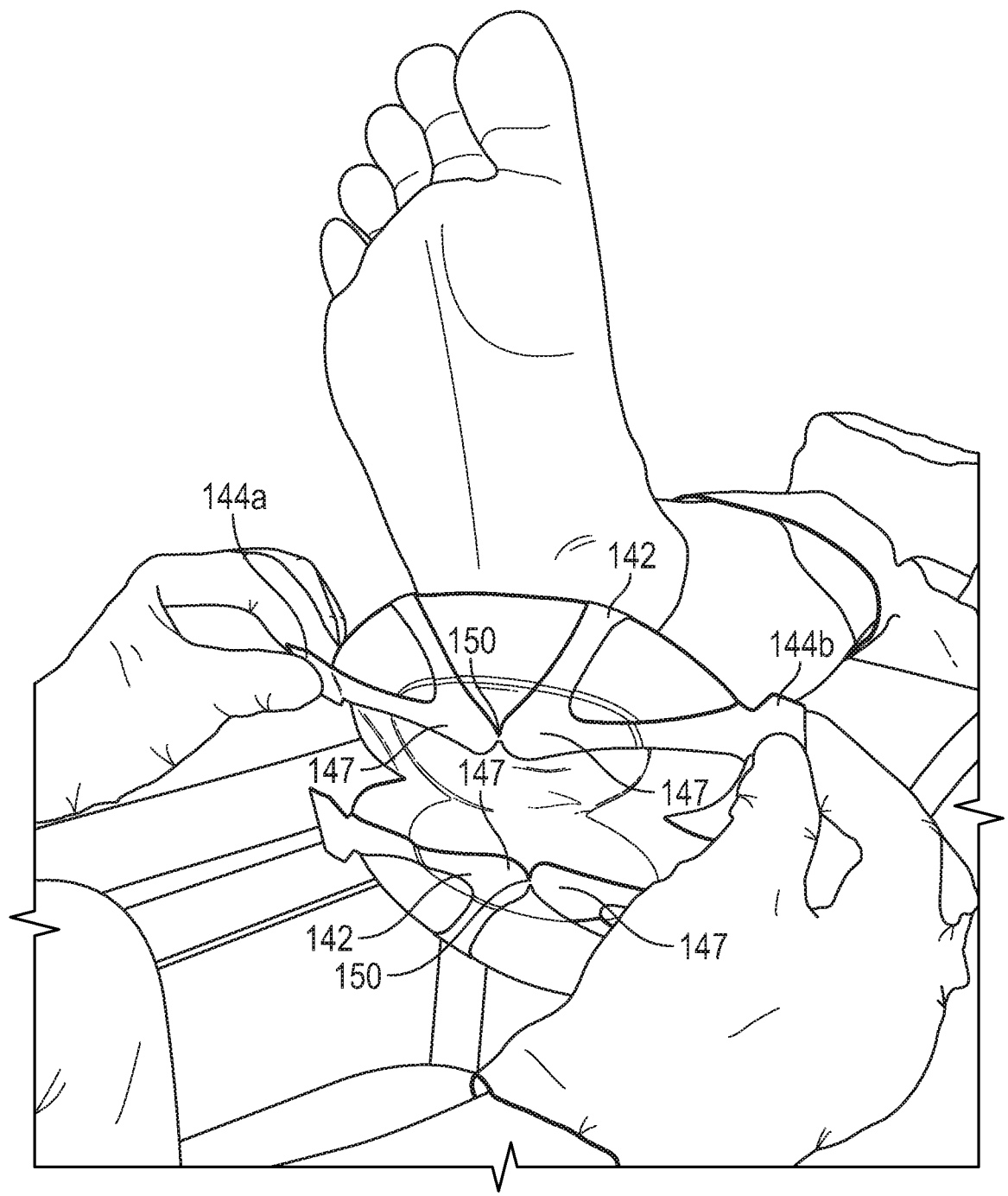
FIGS. 6A-F illustrate one application of the combined wound dressing and delivery system of FIGS. 2A and 2B.
Figure 6B:
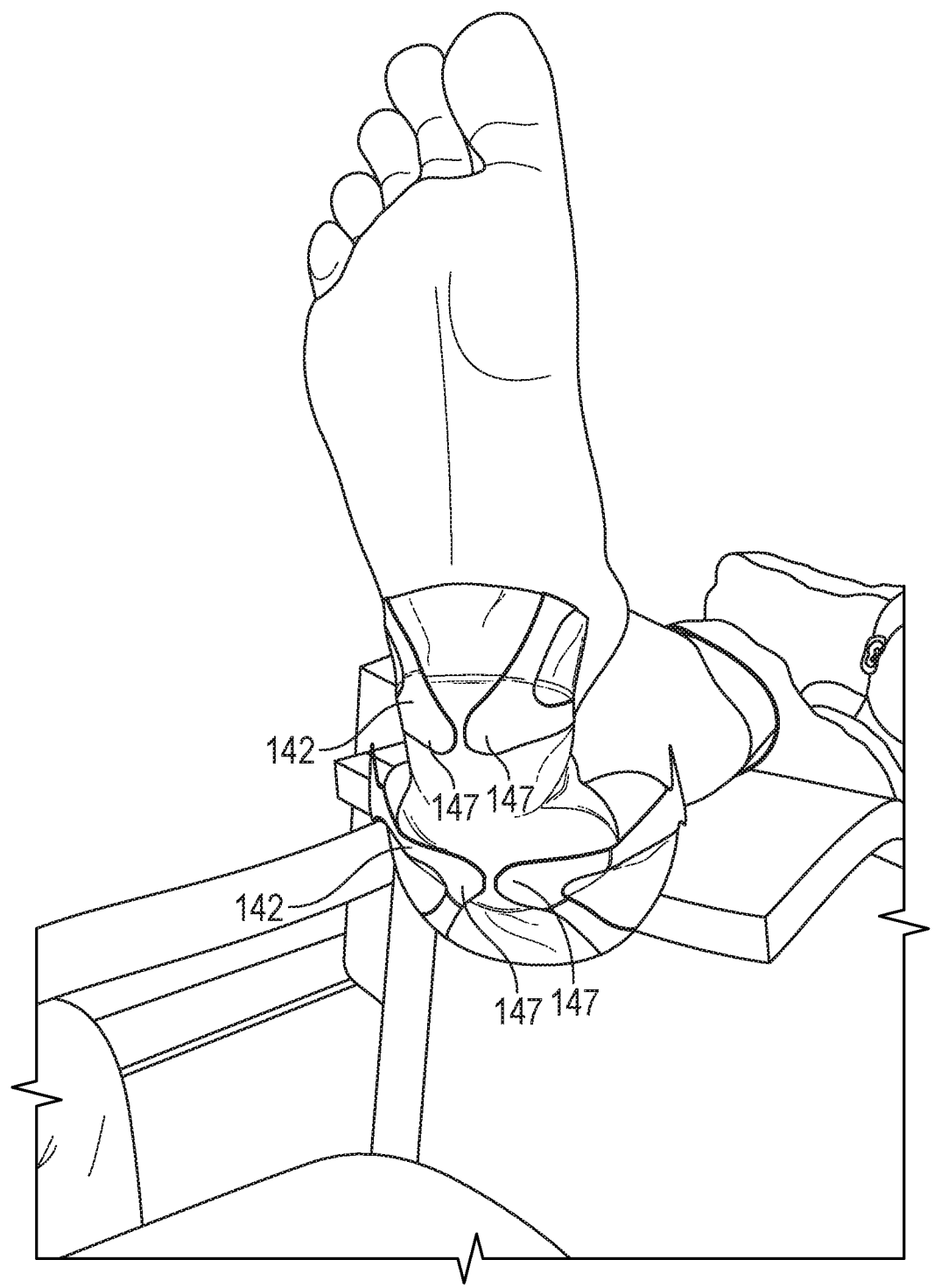
Figure 6C:
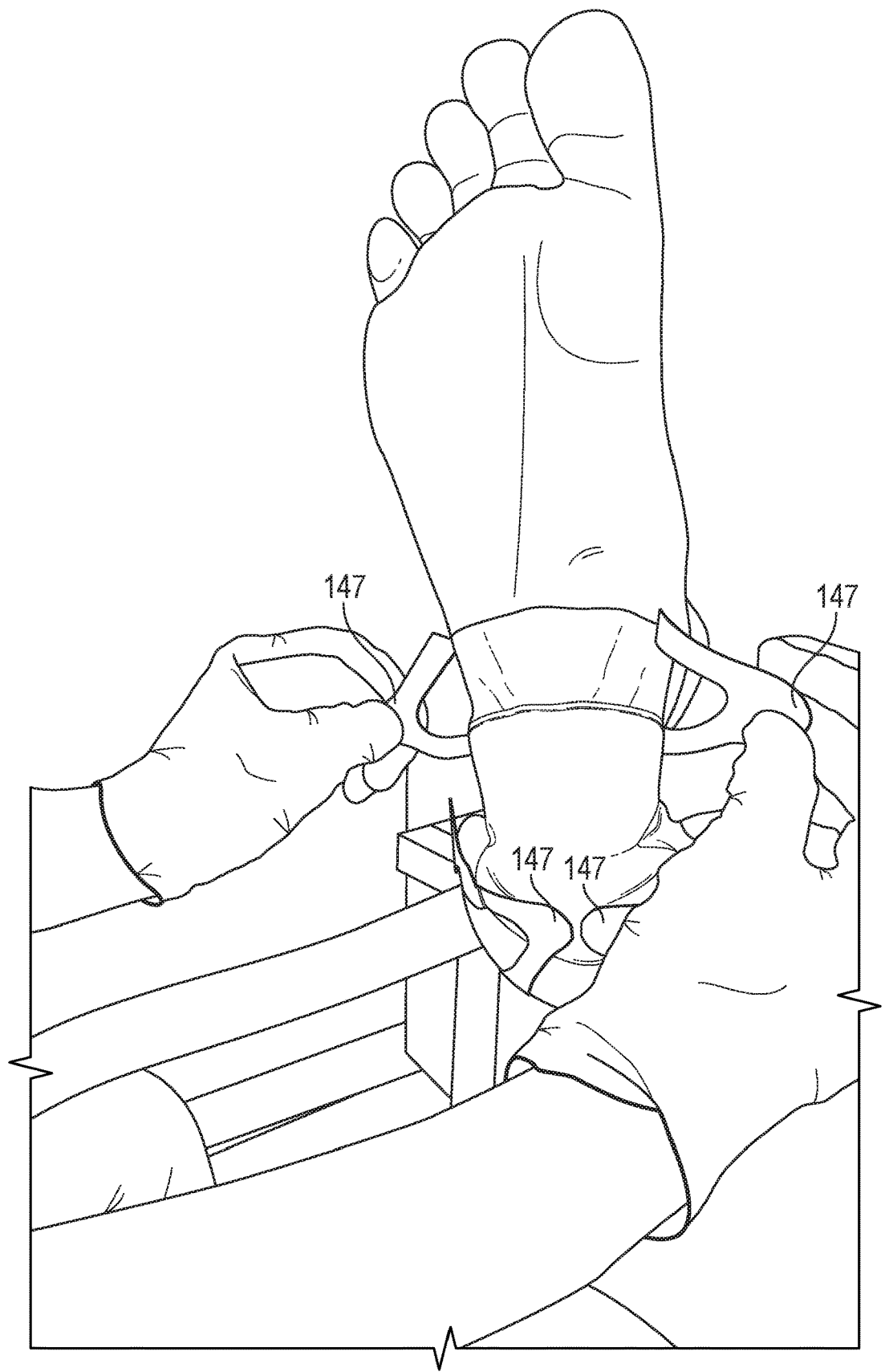
Figure 6D:
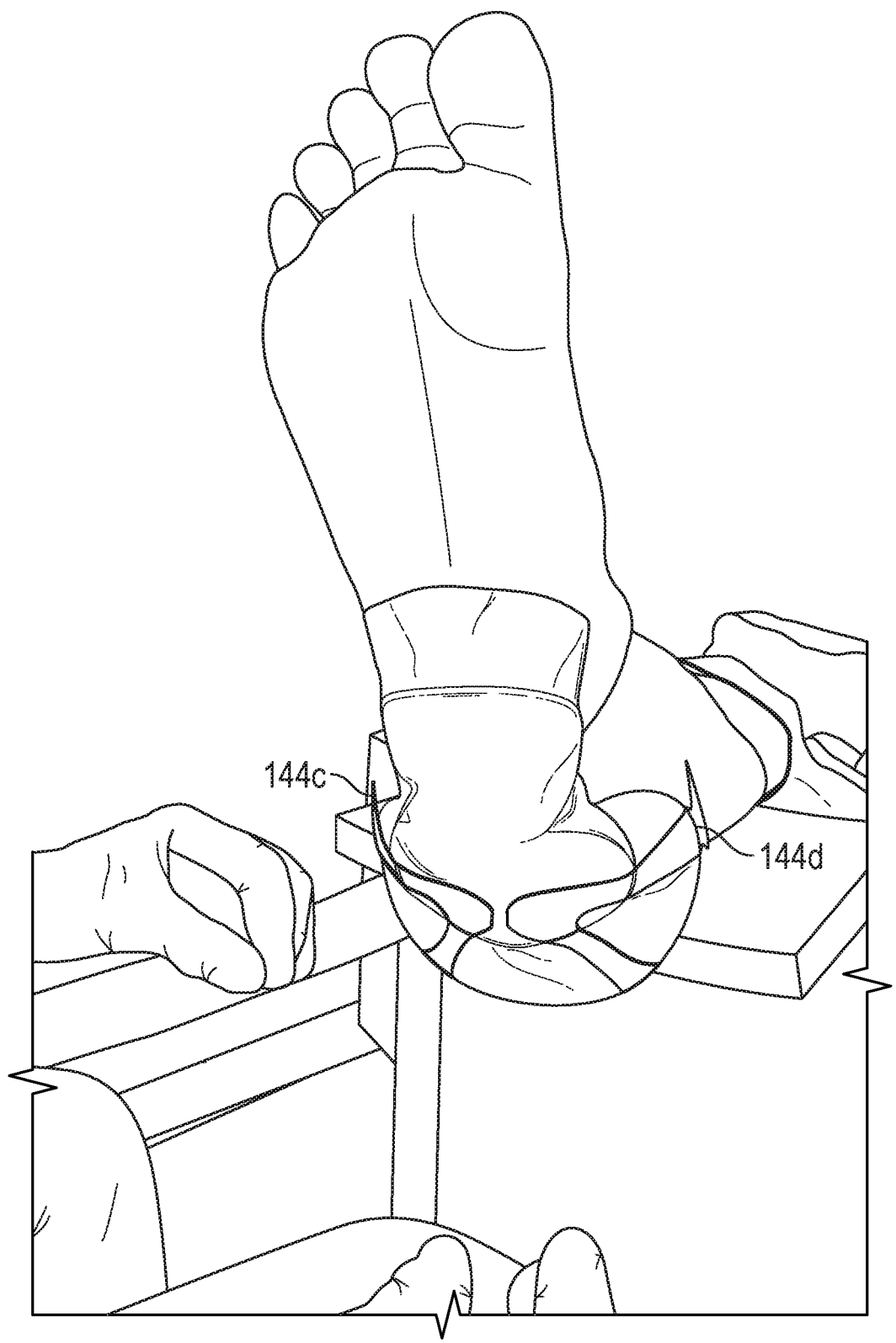
Figure 6E:
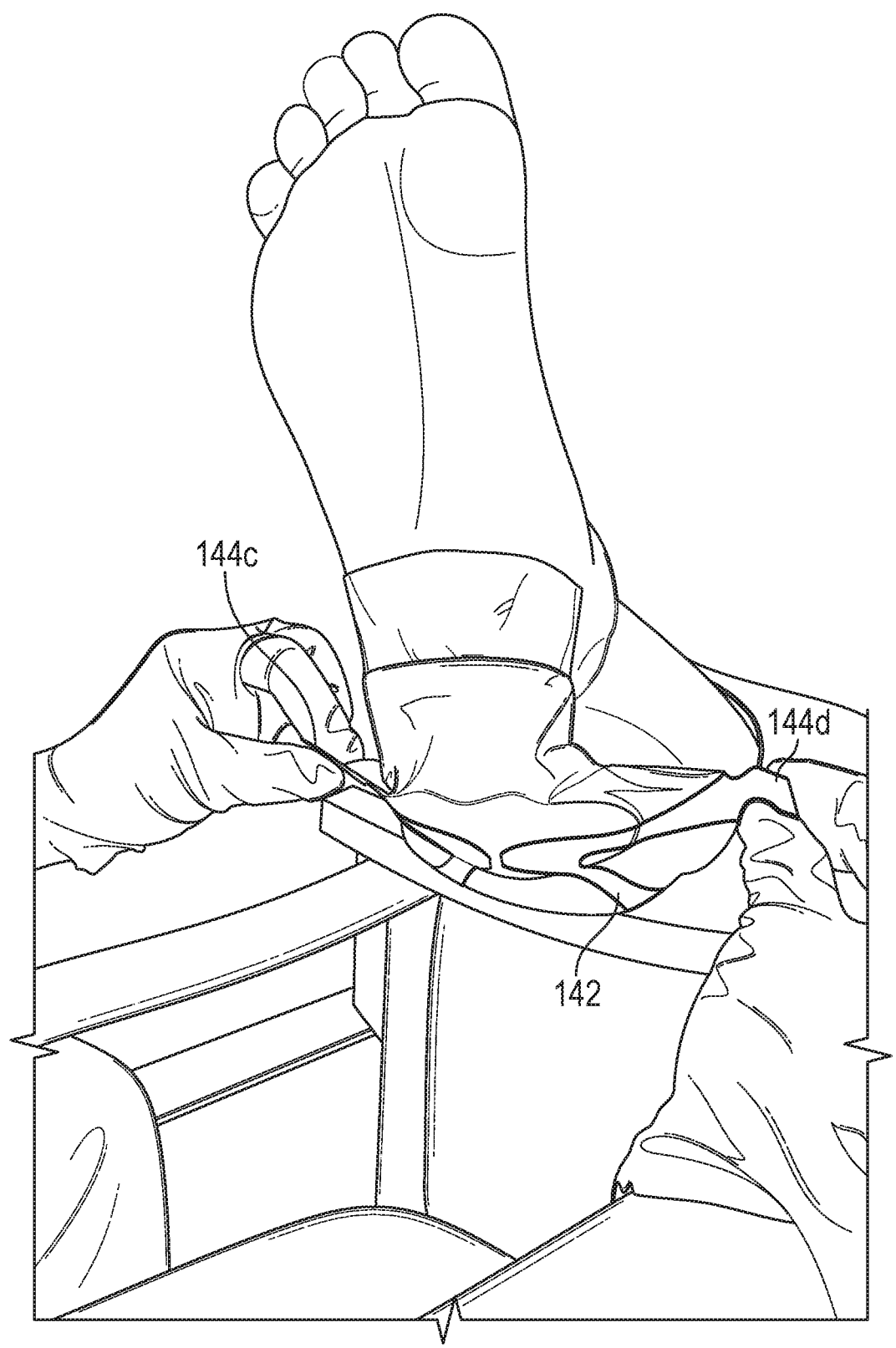
Figure 6F:
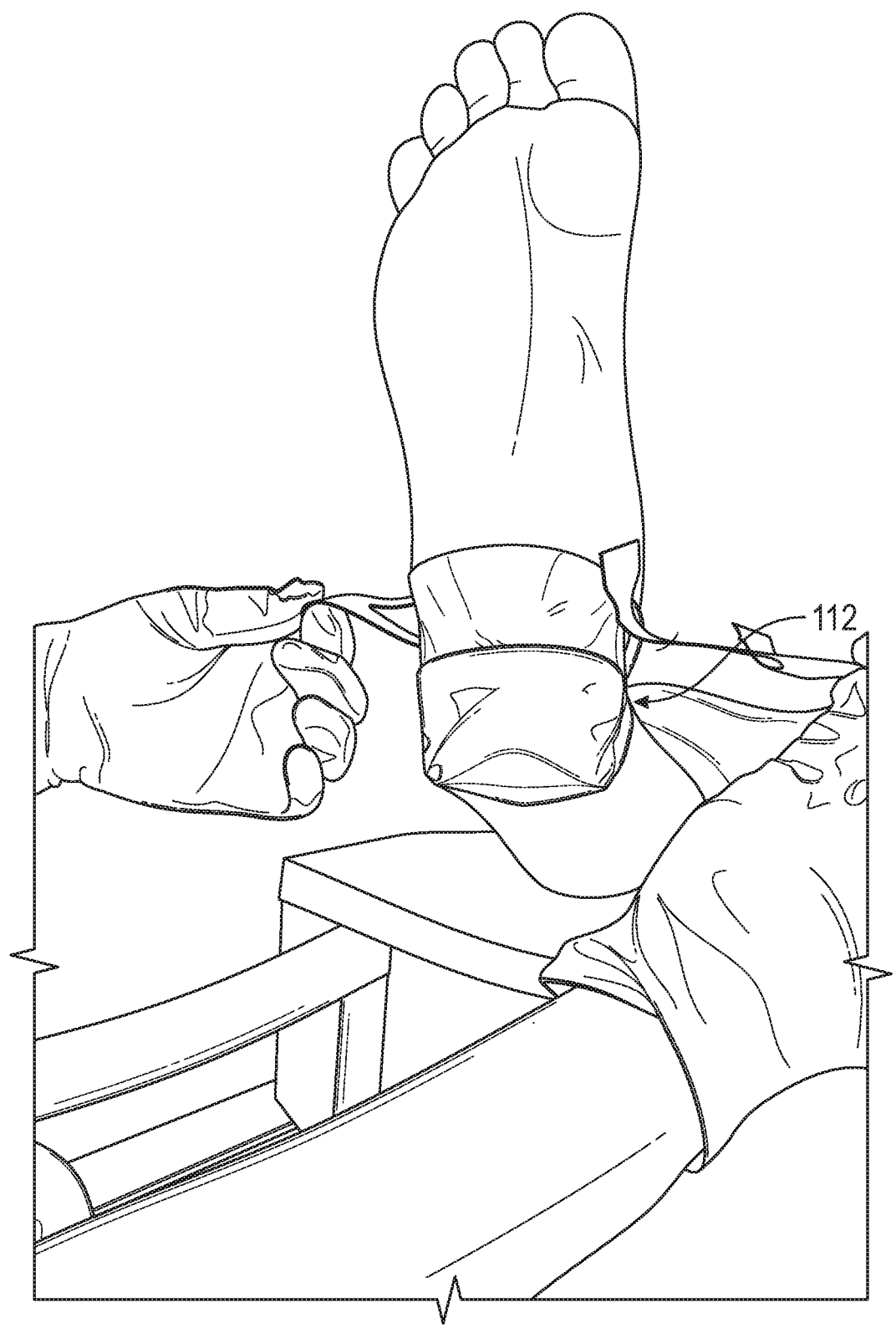

FIGS. 6A-F illustrate one way to use the medical article in FIGS. 2A and 2B to dress a heel wound. As illustrated in FIGS. 6A and 6B, the user grasps tab 144a in one hand and opposing tab 144b in the other hand and wraps one lobe of the dressing around the heel just above the base of the heel. The user then removes the carrier strand 142 over the region of the dressing attached to the heel, as shown if FIG. 6C, by grabbing tabs 147 and peeling each section of strand 142 back towards the perimeter of the dressing. In some instances, the bending of the dressing will break the precut path 150 (if not already broken) causing the tabs 147 to rise off the first major surface of the backing, facilitating removal of the carrier strand 142 from the wound dressing. Removal of a portion of the carrier increases the flexibility of the wound dressing to more freely wrap about the heel. In FIGS. 6D and 6E, the user grabs tab 144c in one hand and opposite tab 144d in the other hand and wraps the remaining portion of the dressing around the heel so that the dressing overlaps on itself to produce a relatively smooth dressing with a secure border to protect the wound site. The remaining carrier strand 142 is then removed as shown in FIG. 6F.

Figure 3A:
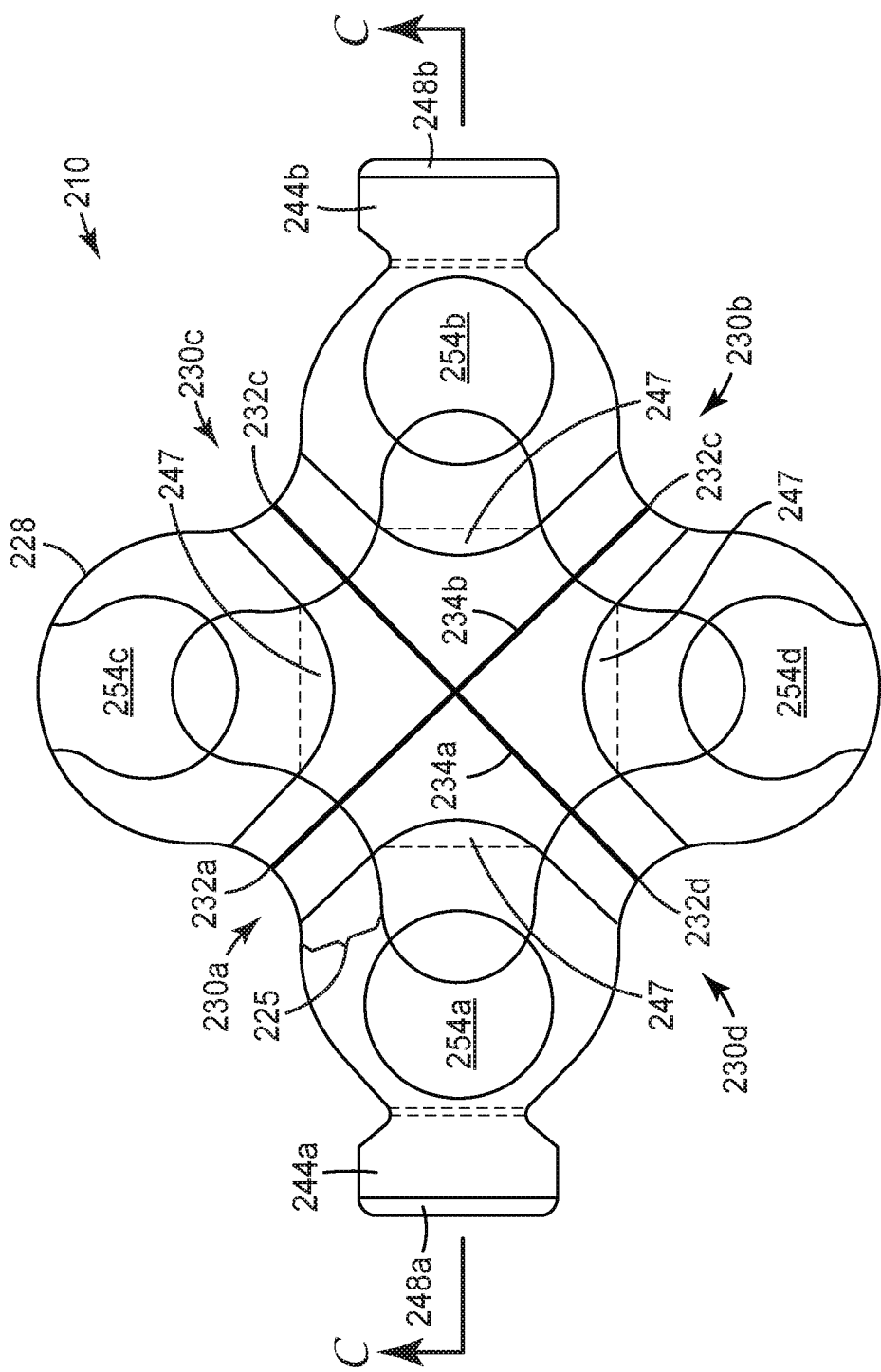
FIG. 3A is a schematic top plan view of a third embodiment of a combined wound dressing and delivery system in the present disclosure.
Figure 3B:
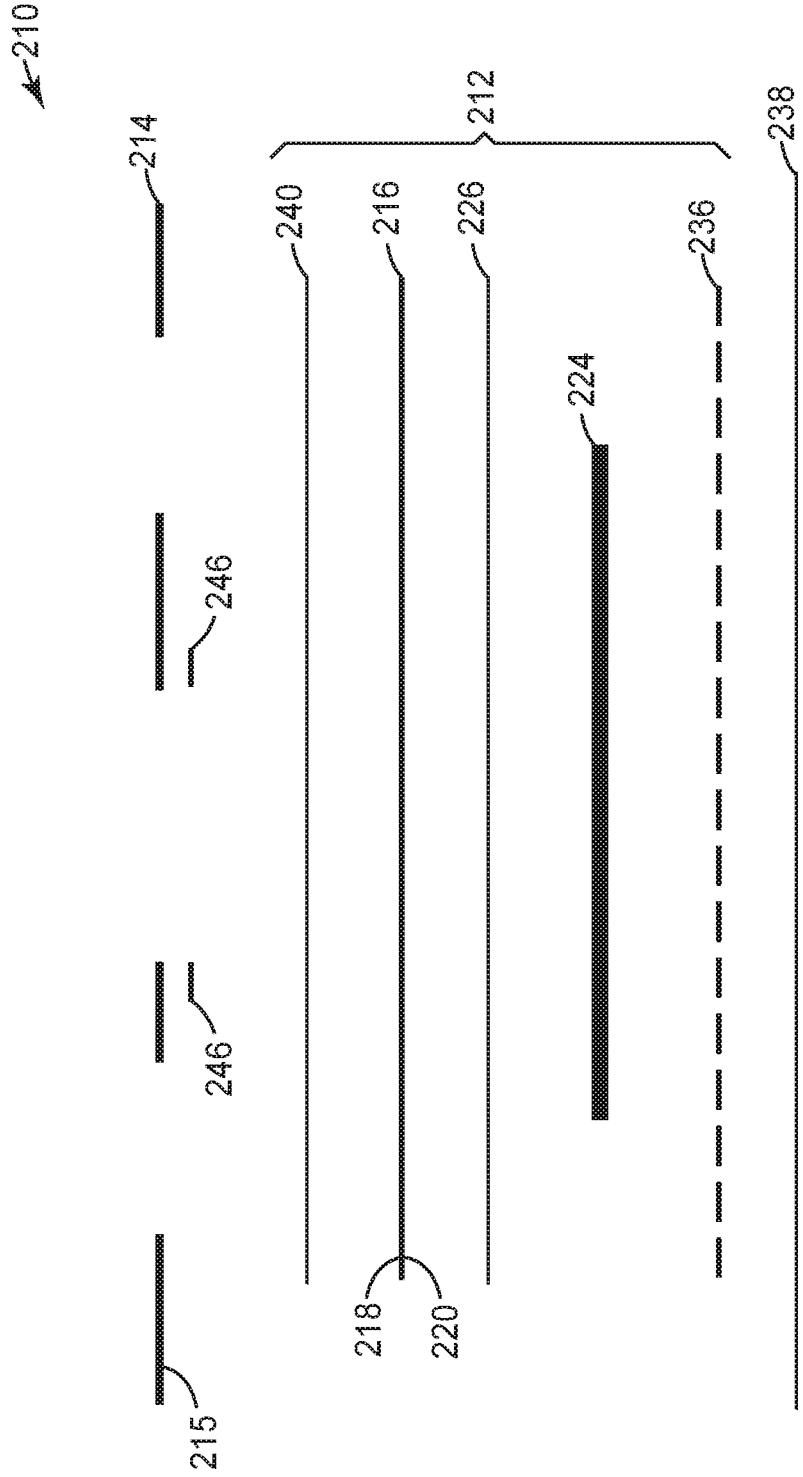
FIG. 3B is a schematic cross-sectional view of the combined wound dressing and delivery system taken along line C-C in FIG. 3A.

FIGS. 3A & 3B illustrate a third embodiment of a medical article 210 in the present disclosure. The medical article 210 comprises a wound dressing 212 having a pseudo-diamond shape and a delivery system or carrier 214. The wound dressing 212 has a similar layered configuration to that described above with respect to FIGS. 1 and 2 but differs in that the dressing 212 in FIG. 3A has four concave features 230a, 230b, 230c, 230d on the perimeter 228 of the dressing 112. The first concave feature 230a has a first local minimum 232a, and the second concave feature 230b has a second local minimum 232b. The first concave feature 230a is located opposite the second concave feature 230b. A first axis 234a extends across the wound dressing 212 from the first local minimum 232a of the first concave feature 230a to the second local minimum 232b of the second concave feature 230b. The third concave feature 230c has a third local minimum 232c, and the fourth concave feature 230d has a fourth local minimum 232d. The third concave feature 230c is located opposite the fourth concave feature 230d. A second axis 234b extends across the wound dressing 212 from the third local minimum 232c to the fourth local minimum 232d in a direction substantially perpendicular to the first axis 234a. The axes 234a, 234b define four quadrants 254a, 254b, 254c, 254d of the wound dressing.

The carrier 214 comprises at least four carrier strands removably attached to the first major surface 218 of the backing 216 that has been preferably treated with a low adhesion coating. The carrier 214 overlies at least a portion of the backing 216 in each quadrant 254a, 254b, 254c, 254d bordered by the first and second axes 234a, 234b but does not overlie the backing 216 along either of the first or second axes 234a, 234b. In some embodiments, 5-50%, more particularly 10-30%, of the backing first major surface 218 surrounding the axes 234a, 234b is free of carrier 214. In an alternative embodiment, the backing first major surface 218 within 0.48 cm (3/16 inch), more preferably 0.64 cm (1/4 inch), of each side of the axes 234a, 234b measured in a direction perpendicular to the axes 234a, 234b is free of carrier 214.

The carrier 214 in FIGS. 3A & 3B overlies at least a portion of the absorbent pad 224 and extends to the perimeter 228 of the wound dressing 212, overlying some, but not all, of the dressing border 225. In some embodiments, the carrier overlies 5-50% of the region defined by the dressing border. In other embodiments, the carrier overlies 5-30% of the region defined by the dressing border.

A portion of the carrier 214 overlying the absorbent pad 224 may optionally include a bond block 246 on a major surface 215 facing the backing 216. The bond block 246 prevents attachment of that portion of the carrier 214 to the backing 216, creating tabs 247 that facilitate removal of the carrier 214 by a user. The user simply grabs the tab 247 and peels the carrier 214 back towards the perimeter 228 of the dressing 212.

In FIG. 3A, the carrier 214 in each of two opposing quadrants 254a, 254b extends past the perimeter 228 of the wound dressing 212 to form a tab 244a, 244b. The tab 244a in one quadrant 254a is located substantially opposite the tab 244b in the other quadrant 254b.

A release liner 238 is attached to the exposed adhesive on the front surface of the dressing. In FIGS. 3A and 3B, the release liner 238 extends beyond the carrier tabs 244a, 244b to form release tabs 248a, 248b. The tabs 248a, 248b of the release liner and the tabs 244a, 244b of the carrier are at least partially unattached, allowing for easy separation of the release liner 238 from the carrier 214 and wound dressing 212.

The medical article 3a and 3b can be applied to wound sites using a similar method to that described above for article in FIGS. 1 and 2.

The articles in FIGS. 1-3 are exemplary embodiments and do not reflect all configuration that would fall under the present invention. For example, the concave feature is illustrated in FIGS. 1A, 2A and 3A as a parabolic structure having a local minimum at the point closest to the center of the wound dressing. However, the sides defining the concave feature need not be smooth and regular. Nor is it necessary that the concave feature be parabolic. The concave feature can have linear sides that define, for example, a triangular, pie-shaped configuration.

In each of the illustrated embodiments, the absorbent pad has the same general shape as the backing. However, the absorbent pad does not need to conform exactly to the shape of the backing in order to operate for its intended application. Similarly, the wound dressing in each of the illustrated embodiments are symmetrical about one or more axes, although they need not be symmetrical.

Although each of the carrier, backing, absorbent pad and facing layer are illustrated by a single layer, it should be understood that each of these components may comprises one or more layers.

The medical articles of the present disclosure can be a variety of sizes, depending upon the particular application. However, the border thickness is dictated primarily by the thickness of the backing, adhesive, and, optionally, the facing layer. The border needs to be thin enough to provide flexibility and conformability for a secure seal but thick enough that in combination with the carrier, it can be handled without wrinkling and sticking to itself. In some embodiments, the thickness of the border, excluding the adhesive in direct contact with a user's skin, ranges from [10-110 μm].

Individual components of the medical article will be further described below.

Carrier

The carrier comprises two or more strands cut from a carrier material. The carrier material is substantially more rigid than the backing to prevent the backing from wrinkling or folding back on itself during application. The carrier can be heat-sealable to the backing, with or without the low adhesion coating described above. In general, the carrier comprises at least one of a polyethylene/vinyl acetate copolymer, a polyvinylacetate coated paper, a polyester film, or a polyethylene film. The carrier can also include other materials such as nonwovens, additional polymer films, or papers attached to at least a portion of the aforementioned polymer films.

Backing

Suitable backings include, for example, nonwoven fibrous webs, woven fibrous webs, knits, and films. The backing can be made up of a single layer of material or multiple layers of one or more materials. The backing is preferably impermeable to liquids but permeable to moisture vapor. In some embodiments, the backing is translucent or transparent (e.g., transparent polymeric elastic film).

The backing is preferably conformable and resilient. For example, the backing can conform to nonplanar anatomical surfaces, such as a heel or a joint. In the case of a joint, the backing can stretch to accommodate movement of the joint, such as flexing an elbow, while providing enough resilience to maintain conformability when the joint is returned to its unflexed position. Preferably, the backing has an ultimate elongation of greater than 200%. More preferably, the backing has an ultimate elongation of greater than 400%.

Exemplary backings can be found, for example, in U.S. Pat. Nos. 5,088,483 and 5,160,315. Particularly preferred backings are elastomeric polyurethane, co-polyester, or polyether block amide films. These films combine the desirable properties of conformability, high moisture vapor permeability, and transparency desired in certain backings.

Adhesive

The adhesive is preferably a pressure sensitive adhesive. While any pressure sensitive adhesive can be used, the preferred pressure sensitive adhesive is reasonably skin compatible and "hypoallergenic". Suitable adhesives include acrylate copolymers described in U.S. Pat. No. RE 24,906. Particularly preferred is a 97:3 iso-octyl acrylate:acrylamide copolymer. Also preferred is an 70:15:15 isooctyl acrylate:ethyleneoxide acrylate:acrylic acid terpolymer, as described in U.S. Pat. No. 4,737,410 (Example 31). Other useful adhesives are described in U.S. Pat. Nos. 3,389,827, 4,112,213, 4,310,509, 4,323,557, and 5,849,325.

Other suitable pressure sensitive adhesives in silicone based adhesives. Silicone adhesives are able to effectively secure dressings to skin and upon removal from the skin produce little or no skin damage. An example of a suitable silicone adhesive is disclosed in PCT Publications WO2010/056541 and WO2010/056543. A radiation cured silicone adhesive is particularly well suited for this application because the extent of crosslinking, and therefore adhesion of the silicone adhesive can be better controlled. Other examples of silicone gel adhesives systems include products marketed with the trade names: Dow Corning MG 7-9850, Wacker SILPURAN® 2110 and 2130, Bluestar SILBIONE® RT Gel 4317 and 4320, Nusil MED-6345 and 6350.

Inclusion of medicaments or antimicrobial agents in the adhesive is also contemplated, an example of which is described in U.S. Pat. Nos. 4,310,509 and 4,323,557.

Preferred pressure sensitive adhesives transmit moisture vapor at a rate greater to or equal to that of human skin. While such a characteristic can be achieved through the selection of an appropriate adhesive or through use of a nonwoven (e.g., melt blown) adhesive (as described in U.S. Pat. Nos. 6,171,985, 6,368,687, and PCT Publication No. WO 99/27975), it is also contemplated in the present invention that other methods of achieving a high relative rate of moisture vapor transmission may be used, such as pattern coating the adhesive on the backing.

If the dressing contains a facing layer, the adhesive may exist on the backing, facing layer or both. Preferably, both the facing layer and backing are precoated with an adhesive layer to both facilitate bonding of the backing to the facing layer (forming a pouch), and bonding of the facing layer to the wound site.

The adhesive may be chosen to be permeable to water or wound exudate, or the adhesive may be pattern coated on the front surface of the wound dressing (i.e. the surface in contact with the wound site, whether it is the front surface of the facing layer or backing) so as to not impede the flow of exudate to the absorbent pad. Alternatively, the adhesive layer may be perforated slit or otherwise modified for the facing layer to provide a fluid path for the exudate.

Absorbent Pad

The construction of the absorbent pad is not particularly limiting. The absorbent pad can be made of one or more layers, and each layer can be made of one or more absorbent materials. Preferred absorbent pads of the present invention are relatively flexible. Flexibility allows for a medical article incorporating the absorbent pad to be easily applied to a bend portion of a body, such as a joint, etc. The absorbent pad can be slit at one of more locations to provide additional flexibility. In some embodiments, the absorbent pad may be translucent or transparent, thus allowing for visual inspection of the wound without removal of the wound dressing.

The absorbent pad can be made of synthetic or natural materials and may include, but is not limited to, woven or nonwoven materials (e.g., woven or nonwoven cotton or rayon), hydrocolloids (e.g., pectin, gelatin, carboxymethylcellulose (CMC), cross-linked carboxymethylcellulose (X-link CMC), cross-linked polyacrylic acid (PAA) and the hydrocolloids described in U.S. Pat. Nos. 5,622,711 and 5,633,010), polymer gels (e.g., hydrogels), foams, collagens, hydrofibers, alginates, and combinations thereof. In some embodiments, the absorbent pad may include a polymeric fabric, a polymeric foam, and combinations thereof. For example, the polymeric fabric may be a nonwoven and the polymeric foam may be the foam used in the TEGADERM foam adhesive dressing available from 3M Company, St. Paul, Minn. In certain embodiments, the polymeric foam is a polyurethane foam.

The absorbent pad may optionally include other components, including one or more active agents, such as pharmacologically active agents. Examples include, but are not limited to, growth factors (e.g., TGF, FGF, PDGF, EGF, etc.), antibacterial agents (e.g., penicillin, neomycin sulfate, sulphonamides, sulfadiazine, silver sulfadiazine, trimethoprim, and other antibiotics, as well as povidone iodine, iodine, silver, silver chloride, and chlorhexidine), antifungal agents (e.g., griseofulvin, chlormidazole hydrochloride, clotrimazole, ketoconazole, miconazole, miconazole nitrate, nistatin, and tolnaftate), disinfectants and antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan), local anaesthetics (e.g., tetracaine, benzocaine, prilocaine, procaine), debriding agents, anti-inflammatory agents (e.g., indomethacin, ketoprofen, dichlofenac, ibuprofen, etc.), astringents, enzymes, nutrients (e.g., vitamins, minerals, oxygen, etc.), drugs for cataplasms (e.g., menthol, camphor, peppermint, *capsicum* extract, capsaicin, etc.), and odor absorbing agents (e.g., zeolites, silicates, chitosans, cyclodextrins, etc.). Active agents can be used alone or as mixtures thereof.

Facing Layer (Optional)

The facing layer is preferably soft, flexible, conformable, non-irritating and non-sensitizing. Suitable facing layers may include, for example, any of the backing materials mentioned above, or a combination thereof. The facing layer may adhere directly to the wound site or be composed of a material that minimizes or prevents attachment to the wound site. The facing layer is preferably liquid permeable and can be made from a liquid permeable material and/or be applied discontinuously (e.g., pattern coated, perforated or slit) so that liquid or exudate from a wound can pass through the facing layer to the absorbent layer.

In one embodiment, the facing layer may be in the form of moisture vapor permeable films, perforated films, woven, non-woven or knit webs or scrims. Any of a variety of polymers may be used, including polyurethane, polyethylene, polypropylene, polyamide or polyester materials.

In yet another embodiment, the facing layer is a porous film having a discontinuous soft, gentle-to-skin adhesive on the surface facing the wound or target site. A second adhesive can be applied on the opposite surface of the facing layer for attachment to the absorbent pad.

As discussed above, it is preferred that the medical articles of the present invention be transparent so that the wound site to which they are applied can be viewed through the wound dressing. Preferred films for use as facing layer and backing that allow visual inspection of the wound site include polyurethane films such as those available under the trade designation ESTANE from B.F. Goodrich, Cleveland, Ohio; elastomeric polyesters such as those available under the trade designation HYTREL from E.I. duPont deNemours & Co., Wilmington, Del.; and, polyether block amides such as those available under the trade designation PEBAX from Elf Altochem North America, Philadelphia, Pa. Other useful films are those describes in U.S. Pat. No. 4,499,896 (Heinecke); U.S. Pat. No. 4,598,004 (Heinecke); and U.S. Pat. No. 5,849,325 (Heinecke et al).

Release Liner

Release liners can be made, for example, of kraft papers, polyethylene, polypropylene, polyester or composites of any of these materials. The liners are preferably coated with release agents such as fluorochemicals or silicones. In some preferred embodiments, the liners are papers, polyolefin films, or polyester films coated with silicone release materials. Examples of commercially available release liners include are POLYSLIK™ silicone release papers available from Loparex (Cary, N.C.); Silicone 1750 coated films from Infiana (Forchheim, Germany), and 3M Scotchpak™ 9741 Release liner from 3M Company (St. Paul, Minn.).

Other combinations of adhesives and liners are contemplated for use with embodiments according to the present invention. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the Handbook of Pressure Sensitive Adhesive Technology, Van Nostrand-Reinhold, 1982, pp. 384-403. U.S. Pat. No. 4,472,480 also describes considerations pertinent to the selection of a perfluoropolyether release liner.

Method of Manufacture

Figure 4:
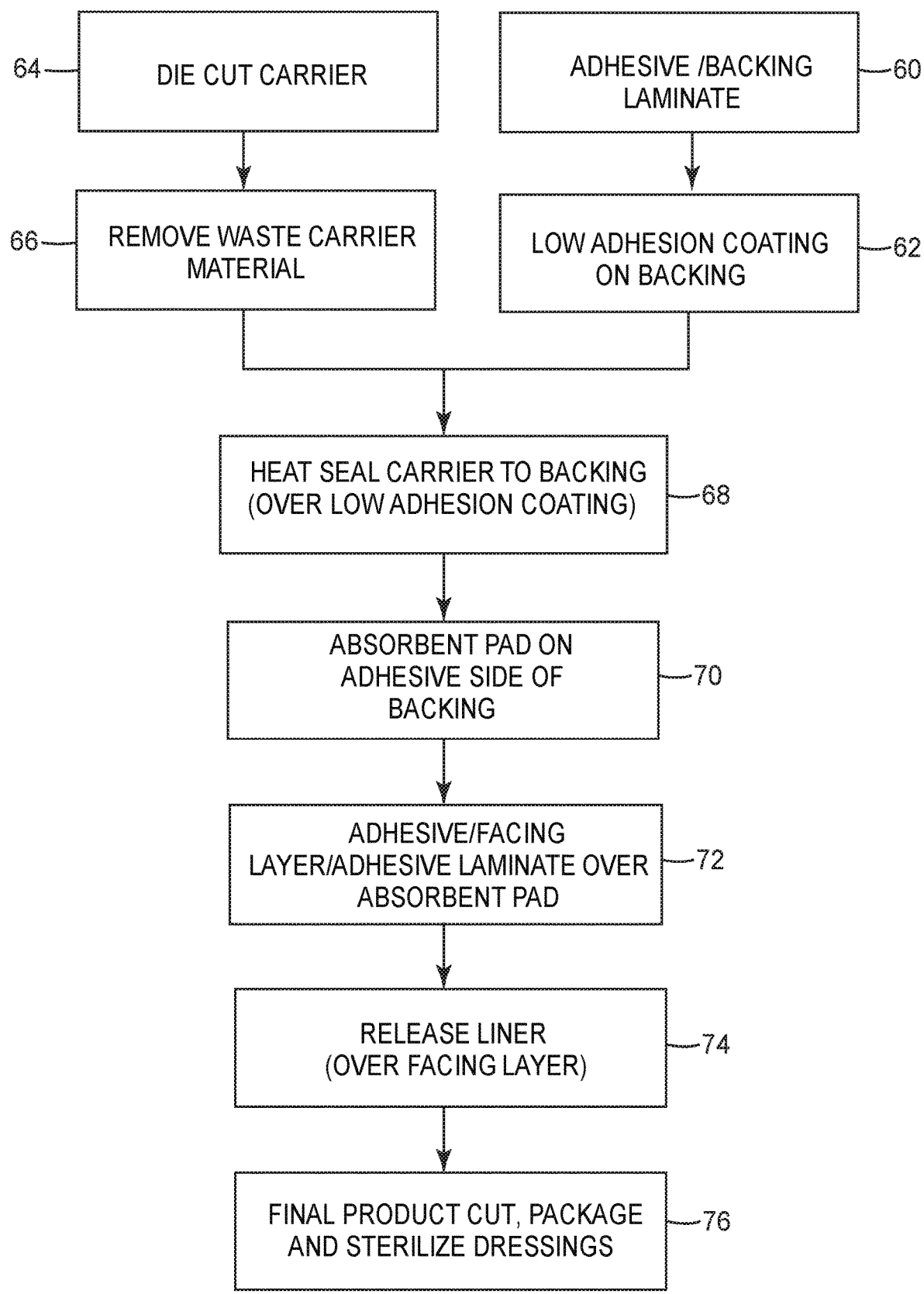
FIG. 4 is a flow chart of one method of manufacturing the articles according to the present invention.

Methods for manufacturing the medical articles of the present disclosure are well known to those skilled in the art. FIG. 4 outlines one such method using the components described above.

An web comprising an adhesive/backing laminate, such as a single-sided tape, is provided in 60. A low adhesion coating may optionally be applied in 62 to the back surface (i.e., non-adhesive surface) of the adhesive/backing laminate to provide the tape-over feature of the resultant dressing, as well as to minimize surface friction due to linen which also reduces unwanted removal of the dressings.

Separately, the carrier is die cut in 64 according to a predetermine pattern. In the preferred embodiments, the die cutting is accomplished using rotary die cutting equipment. Waste carrier material can be removed in 66 from the carrier strands using a number of known methods, including the use of vacuum, air pressure, gravity, and nip rolls having a small diameter.

After the low adhesion coating step 62, the die cutting step 64, and waste carrier removal step 66 are completed, the carrier (or carrier strands) is heat sealed in 68 to the surface of the backing, over the low adhesion coating.

It will be understood that although steps 60/62 and 64/66 are depicted as occurring simultaneously in FIG. 4, they could be performed sequentially and are shown simultaneously only for convenience.

An alternate preferred method involves performing the heat sealing step 68 before the die cutting and waste removal steps 64 and 66. In that method, only the portions of the carrier material corresponding to the carrier strands are heat sealed to the backing so that the waste portions of the carrier can be removed without difficulty. In addition, the die cutting step 64 would require control depth die cutting to avoid cutting through the backing when the carrier strands are cut from the carrier material.

After the waste carrier material has been removed in step 66 and the heat sealing step 68 has been performed, absorbent pads are cut to size and bond to the adhesive side of the adhesive/backing laminate web in 70. Preferably the absorbent pads is smaller in dimensions than the backing so that the results product is and island dressing.

A perforated adhesive/facing layer/adhesive laminate, such as a perforated double-sided tape, is applied over the backing and absorbent pad in 72. Preferably the facing layer is contiguous with the adhesive/backing laminate. A release liner in 74 is then applied to the exposed adhesive on the facing layer.

The result of steps 60, 62, 64, 66, 68, 70, 72 and 74 is an adhesive composite web comprising a carrier heat sealed to the low adhesion coated side of an adhesive/backing laminate web, absorbent pads adhesively bonded to the backing at spaced intervals along the adhesive/backing laminate web, a facing layer having an adhesive on both sides overlying the absorbent pad and adhesive/backing laminate web, and a web of release liner covering the exposed adhesive on the facing layer.

The only remaining step is to convert the adhesive composite web into finished product in 76. That web is preferably directed into a rotary die sheeting station which cuts the dressings out of the web and pulls the weed or waste material away for disposal. Preferably, the individual dressings are fed directly into a packaging station which packages the dressings for sterilization and delivery to customers.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention.

Thus, the invention provides, among other things, a medical article comprising a conformable wound dressing a delivery system. Various features and advantages of the invention are set forth in the following claims.

What is claimed is:

1. A medical article comprising:
    a wound dressing physically defined by a wound dressing perimeter having at least one concave feature that exhibits a local minimum, the wound dressing comprising:
    a backing having a first major backing surface and a second major backing surface;
    an adhesive on the second major backing surface;
    an absorbent pad having a first major pad surface and a second major pad surface, the first major pad surface proximate the second major backing surface, the absorbent pad defined by an absorbent pad perimeter,
        wherein the backing extends beyond the absorbent pad perimeter;
    a symmetry axis extending from the local minimum to the wound dressing perimeter opposite the local minimum; and
    a carrier comprising at least two carrier strands removably attached to the first major backing surface,
        wherein at least a portion of the carrier extends to the wound dressing perimeter,
        wherein the carrier overlies at least a portion of the absorbent pad, and
        wherein the carrier overlies at least a portion of the backing on each side of the symmetry axis but does not overlie the backing along the symmetry axis.

2. The article of claim 1, wherein 5-50% of the first major backing surface surrounding the symmetry axis is free of carrier.

3. The article of claim 1, wherein the carrier on each side of the symmetry axis extends past the wound dressing perimeter of the to form a tab.

4. The article of claim 1, wherein the carrier on each side of the symmetry axis extends past the wound dressing perimeter to form a tab, the tab on one side of the symmetry axis located opposite the tab on the other side of the symmetry axis, both tabs extending in a direction perpendicular to the symmetry axis.

5. The article of claim 1, the wound dressing further comprising a second concave feature having a second local minimum, wherein the second concave feature is located opposite the first concave feature, and the symmetry axis extends across the wound dressing from the first local minimum to the second local minimum.

6. The article of claim 5, wherein 5-50% of the first major backing surface surrounding the symmetry axis is free of carrier.

7. The article of claim 5, wherein the carrier on each side of the symmetry axis extends past the wound dressing perimeter to form a pair of tabs, wherein one tab is located opposite the other tab, and each tab extends in a direction parallel to the symmetry axis.

8. The article of claim 5, the wound dressing further comprising a third concave feature having a third local minimum and a fourth concave feature having a fourth local minimum, wherein the third concave feature is located opposite the fourth concave feature and a symmetry axis extends across the wound dressing from the third local minimum to the fourth local minimum, the symmetry axes being substantially perpendicular to one another, and wherein the carrier overlies at least a portion of the backing in each quadrant bordered by the symmetry axes but does not overlie the backing along either of the symmetry axes.

9. The article of claim 8, wherein 5-50% of the first major backing surface surrounding the symmetry axes are free of carrier.

10. The article of claim 8, wherein the carrier in each of two opposite quadrants extends past the wound dressing perimeter to form a tab, the tab in one quadrant located opposite the tab in the other quadrant.

11. The article of claim 1, the wound dressing further comprising a border defined by a portion of the backing that extends beyond the absorbent pad, and the carrier overlies 5-40% of the border.

12. The article of claim 1, the wound dressing further comprising a border defined by a portion of the backing that extends beyond the absorbent pad, and the carrier overlies 5-25% of the border.

13. The article of claim 1, the portion of the carrier that overlies the absorbent pad comprising a bond block on a surface facing the backing to prevent attachment of the portion of the carrier to the backing and facilitate removal of the carrier by a user.

14. The article of claim 1, the carrier further comprising a precut path so that the carrier can be removed in smaller segments.

15. The article of claim 1, further comprising a low adhesion coating on the first major backing surface, such that at least a portion of the low adhesion coating is sandwiched between the carrier and the first major backing surface.

16. The article of claim 1, the wound dressing further comprising a facing layer having a first major facing surface and a second major facing surface, the first major facing surface proximate the second major facing surface of at least one of the backing, absorbent pad and combinations thereof.

17. The article of claim 16, wherein the facing layer is contiguous with the backing.

18. The article of claim 16, wherein the facing layer is perforated.

\* \* \* \* \*